United States Patent [19]
Wnendt et al.

[11] Patent Number: 6,133,011
[45] Date of Patent: Oct. 17, 2000

[54] CHIMERIC PROTEINS HAVING FIBRINOLYTIC AND THROMBIN-INHIBITING PROPERTIES

[75] Inventors: Stephan Wnendt; Gerd Josef Steffens, both of Aachen; Elke Janocha, Linnich; Regina Heinzel-Wieland, Darmstadt, all of Germany

[73] Assignee: Gruenenthal GmbH, Aachen, Germany

[21] Appl. No.: 08/967,024

[22] Filed: Nov. 10, 1997

Related U.S. Application Data

[63] Continuation of application No. 08/563,649, Nov. 28, 1995.

[30] Foreign Application Priority Data

Nov. 30, 1994 [DE] Germany .............................. 44 42 665

[51] Int. Cl.[7] .............................. A61K 38/36; C12N 9/72; C12N 15/58; C12N 15/62
[52] U.S. Cl. ...................... 435/212; 435/69.7; 435/252.3; 435/252.33; 435/320.1; 424/94.64; 536/23.4
[58] Field of Search .................................... 435/69.6, 212, 435/252.3, 255.33, 320.1, 69.7; 424/94.64; 536/23.4

[56] References Cited

U.S. PATENT DOCUMENTS

| | | | |
|---|---|---|---|
| 5,288,490 | 2/1994 | Budzynski et al. ................... | 424/94.64 |
| 5,637,503 | 6/1997 | Brigelius-Flohe et al. .......... | 435/320.1 |
| 5,681,721 | 10/1997 | Steffens et al. ........................ | 435/69.6 |
| 5,747,291 | 5/1998 | Steffens et al. ........................ | 435/69.6 |

FOREIGN PATENT DOCUMENTS

| | | |
|---|---|---|
| 350692 | 6/1989 | European Pat. Off. . |
| 383417 | 8/1990 | European Pat. Off. . |
| 408945 | 1/1991 | European Pat. Off. . |
| 669394 A1 | 8/1995 | European Pat. Off. . |
| WO 91/09125 | 6/1991 | WIPO . |
| WO 92/10575 | 6/1992 | WIPO . |
| WO 92/18139 | 10/1992 | WIPO . |

OTHER PUBLICATIONS

Phaneuf et al., 70(4) Thromb. Haemost. 481–87 (1994).
Riccio et al, 13(8) Nucleic Acids Res. 2759–71 (1985).
Maraganore et al., 264(15) J. Biol. Chem. 8692–98 (1989).
Yue et al., 5(1) Prot. Engineering 77–85 (1992).
Liu et al. 266(26) J. Biol. Chem. 16977–80 (1991).
Bowie et al., 247 Science 1306–1310 (1990).
Taylor, Introduction—Patterns, Predictions and Problems in "Patterns in Protein Sequence and Structure," pp. 1–9, Springer–Verlag, New York (Taylor, ed. 1992).
Brigelius–Flohe et al., *Appl. Microbiol. Biotech.* 36, 640–649 (1992).
Brommer and Meijer, *Thromb. Haemostas.* 70, 995–997 (1993).
Collen and Lijnen, *Blood* 78, 3114–3124 (1991).
Collen and Van De Werf, *Circulation,* 87, 1850–1857 (1993).
Dodt et al., *Biol. Chem. Hoppe–Seyler* 366, 379–385 (1985).
Furie and Furie, *New Engl J. Med,* 326, 800–806 (1992).

Gardell et al., *Circulation* 84, 244–253 (1991).
Gardell et al., *J. Biol. Chem.* 264, 17947–17952 (1989).
Gruber et al., *Circulation* 84, 2454–2462 (1991).
Gunzler et al., *Hoppe–Seyler's Z. Physiol. Chem.* 363, 1155–1165 (1982).
Keyt et al., *Proc. Natl. Acad Sci.* 91, 3670–3674 (1994).
Cataldi et al., *Febs Lett.* 269, 465–468 (1990).
Krstenansky et al., *J. Med. Chem* 30, 1688–1691 (1987).
Lijnen et al., *J Biol. Chem.* 261, 1253–1258 (1986).
Maraganore et al., *Biochemistry* 29, 7095–7101 (1990).
Martin et al., *J. Am. Coll. Cardiol.* 22, 914–920 (1993).
Refino et al., *Thromb. Haemost.* 70, 313–319 (1993).
Rydel et al., *Science* 249, 277–280 (1990).
Schlott et al., *Bio/Technology,* 12, 185–189 (1994).
Schneider, *Thromb. Res.* 64, 667–687 (1991).
Steffens et al., *Hoppe–Seyler's Z. Physiol. Chem.* 363, 1043–1058 (1982).
Stone and Hofsteenge, *Prot. Engineering* 2, 295–300 (1991).
Stump et al., *J. Biol. Chem.* 261, 1267–1269 (1986).
Vlasuk et al., *Circulation* 84, Suppl. 11–467 (1991) (Abstract No. 1859).
Vu et al., *Nature* 253, 674–677 (1991).
Winkler et al., *Biochemistry* 25, 4041–4045 (1986).
Wun et al., *J. Biol. Chem.* 257, 3276–3283 (1982).
Heyneker et al., Proceedings of the IVth International Symposium on Genetics of Industrial Microorganisms 1982, pp. 214–221.
Bode and Huber, in "Molecular Aspects of Inflammation", Berlin, Heidelberg 103–I15 (1991), Sies, H., et al. Eds., Springer–Verlag.
Goto et al., *Angiology* 45, 273–281 (1994).
Martin et al., *J. Cardiovasc. Pharmacol.* 18, 111–119 (1991).
Szczeklik et al., *Arterioscl. Thromb.* 12, 548–553 (1992).
Tebbe et al., *Z. Kardiol.* 80, Suppl. 3, 32 (1991).
Yao et al., *Am. J. Physiol* 262 (*Heart Circ. Physiol.* 31) H 347–H 379 (1992).
Excerpt from Protein Engineering, Stephan Wnendt et al., Construction and structure–activity relationships of chimeric prourokinase derivatives with intrinsic thrombin–inhibitory potential, vol. 9, No. 2, pp. 213–223, 1996.
Derwent Abstract of Japanese Publication No. 5–078397, Mar. 30, 1993.

*Primary Examiner*—Ponnathapu Achutamurthy
*Assistant Examiner*—William W. Moore
*Attorney, Agent, or Firm*—Evenson, McKeown, Edwards & Lenahan, P.L.L.C.

[57] ABSTRACT

Chimeric proteins with fibrinolytic and thrombin-inhibiting properties having a plasminogen-activating amino acid sequence which is linked at its C-terminal end to a thrombin-inhibiting amino acid sequence.

7 Claims, 14 Drawing Sheets

Figure 13: Amino acid sequence of M37

Met-Ser-Lys-Thr-Cys-Tyr-Glu-Gly-Asn-Gly-His-Phe-Tyr-Arg-
Gly-Lys-Ala-Ser-Thr-Asp-Thr-Met-Gly-Arg-Pro-Cys-Leu-Pro-
Trp-Asn-Ser-Ala-Thr-Val-Leu-Gln-Gln-Thr-Tyr-His-Ala-His-
Arg-Ser-Asp-Ala-Leu-Gln-Leu-Gly-Leu-Gly-Lys-His-Asn-Tyr-
Cys-Arg-Asn-Pro-Asp-Asn-Arg-Arg-Arg-Pro-Trp-Cys-Tyr-Val-
Gln-Val-Gly-Leu-Lys-Pro-Leu-Val-Gln-Glu-Cys-Met-Val-His-
Asp-Cys-Ala-Asp-Gly-Lys-Lys-Pro-Ser-Ser-Pro-Pro-Glu-Glu-
Leu-Lys-Phe-Gln-Cys-Gly-Gln-Lys-Thr-Leu-Arg-Pro-Arg-Phe-
Lys-Ile-Ile-Gly-Gly-Glu-Phe-Thr-Thr-Ile-Glu-Asn-Gln-Pro-
Trp-Phe-Ala-Ala-Ile-Tyr-Arg-Arg-His-Arg-Gly-Gly-Ser-Val-
Thr-Tyr-Val-Cys-Gly-Gly-Ser-Leu-Ile-Ser-Pro-Cys-Trp-Val-
Ile-Ser-Ala-Thr-His-Cys-Phe-Ile-Asp-Tyr-Pro-Lys-Lys-Glu-
Asp-Tyr-Ile-Val-Tyr-Leu-Gly-Arg-Ser-Arg-Leu-Asn-Ser-Asn-
Thr-Gln-Gly-Glu-Met-Lys-Phe-Glu-Val-Glu-Asn-Leu-Ile-Leu-
His-Lys-Asp-Tyr-Ser-Ala-Asp-Thr-Leu-Ala-His-His-Asn-Asp-
Ile-Ala-Leu-Leu-Lys-Ile-Arg-Ser-Lys-Glu-Gly-Arg-Cys-Ala-
Gln-Pro-Ser-Arg-Thr-Ile-Gln-Thr-Ile-Cys-Leu-Pro-Ser-Met-
Tyr-Asn-Asp-Pro-Gln-Phe-Gly-Thr-Ser-Cys-Glu-Ile-Thr-Gly-
Phe-Gly-Lys-Glu-Asn-Ser-Thr-Asp-Tyr-Leu-Tyr-Pro-Glu-Gln-
Leu-Lys-Met-Thr-Val-Val-Lys-Leu-Ile-Ser-His-Arg-Glu-Cys-
Gln-Gln-Pro-His-Tyr-Tyr-Gly-Ser-Glu-Val-Thr-Thr-Lys-Met-
Leu-Cys-Ala-Ala-Asp-Pro-Gln-Trp-Lys-Thr-Asp-Ser-Cys-Gln-
Gly-Asp-Ser-Gly-Gly-Pro-Leu-Val-Cys-Ser-Leu-Gln-Gly-Arg-
Met-Thr-Leu-Thr-Gly-Ile-Val-Ser-Trp-Gly-Arg-Gly-Cys-Ala-
Leu-Lys-Asp-Lys-Pro-Gly-Val-Tyr-Thr-Arg-Val-Ser-His-Phe-
Leu-Pro-Trp-Ile-Arg-Ser-His-Thr-Lys-Glu-Glu-Asn-Gly-Leu-
Ala-Leu-Ser-Pro-Val-Val-Ala-Phe-Pro-Arg-Pro-Phe-Leu-Leu-
Arg-Asn-Pro-Gly-Asp-Phe-Glu-Glu-Ile-Pro-Glu-Glu-Tyr-Leu-
Gln (SEQ ID NO:24)

Figure 14: Amino acid sequence of M38

Met-Ser-Lys-Thr-Cys-Tyr-Glu-Gly-Asn-Gly-His-Phe-Tyr-Arg-
Gly-Lys-Ala-Ser-Thr-Asp-Thr-Met-Gly-Arg-Pro-Cys-Leu-Pro-
Trp-Asn-Ser-Ala-Thr-Val-Leu-Gln-Gln-Thr-Tyr-His-Ala-His-
Arg-Ser-Asp-Ala-Leu-Gln-Leu-Gly-Leu-Gly-Lys-His-Asn-Tyr-
Cys-Arg-Asn-Pro-Asp-Asn-Arg-Arg-Arg-Pro-Trp-Cys-Tyr-Val-
Gln-Val-Gly-Leu-Lys-Pro-Leu-Val-Gln-Glu-Cys-Met-Val-His-
Asp-Cys-Ala-Asp-Gly-Lys-Lys-Pro-Ser-Ser-Pro-Pro-Glu-Glu-
Leu-Lys-Phe-Gln-Cys-Gly-Gln-Lys-Thr-Leu-Arg-Pro-Arg-Phe-
Lys-Ile-Ile-Gly-Gly-Glu-Phe-Thr-Thr-Ile-Glu-Asn-Gln-Pro-
Trp-Phe-Ala-Ala-Ile-Tyr-Arg-Arg-His-Arg-Gly-Gly-Ser-Val-
Thr-Tyr-Val-Cys-Gly-Gly-Ser-Leu-Ile-Ser-Pro-Cys-Trp-Val-
Ile-Ser-Ala-Thr-His-Cys-Phe-Ile-Asp-Tyr-Pro-Lys-Lys-Glu-
Asp-Tyr-Ile-Val-Tyr-Leu-Gly-Arg-Ser-Arg-Leu-Asn-Ser-Asn-
Thr-Gln-Gly-Glu-Met-Lys-Phe-Glu-Val-Glu-Asn-Leu-Ile-Leu-
His-Lys-Asp-Tyr-Ser-Ala-Asp-Thr-Leu-Ala-His-His-Asn-Asp-
Ile-Ala-Leu-Leu-Lys-Ile-Arg-Ser-Lys-Glu-Gly-Arg-Cys-Ala-
Gln-Pro-Ser-Arg-Thr-Ile-Gln-Thr-Ile-Cys-Leu-Pro-Ser-Met-
Tyr-Asn-Asp-Pro-Gln-Phe-Gly-Thr-Ser-Cys-Glu-Ile-Thr-Gly-
Phe-Gly-Lys-Glu-Asn-Ser-Thr-Asp-Tyr-Leu-Tyr-Pro-Glu-Gln-
Leu-Lys-Met-Thr-Val-Val-Lys-Leu-Ile-Ser-His-Arg-Glu-Cys-
Gln-Gln-Pro-His-Tyr-Tyr-Gly-Ser-Glu-Val-Thr-Thr-Lys-Met-
Leu-Cys-Ala-Ala-Asp-Pro-Gln-Trp-Lys-Thr-Asp-Ser-Cys-Gln-
Gly-Asp-Ser-Gly-Gly-Pro-Leu-Val-Cys-Ser-Leu-Gln-Gly-Arg-
Met-Thr-Leu-Thr-Gly-Ile-Val-Ser-Trp-Gly-Arg-Gly-Cys-Ala-
Leu-Lys-Asp-Lys-Pro-Gly-Val-Tyr-Thr-Arg-Val-Ser-His-Phe-
Leu-Pro-Trp-Ile-Arg-Ser-His-Thr-Lys-Glu-Glu-Asn-Gly-Leu-
Ala-Leu-Ser-Pro-Val-Val-Ala-Phe-Pro-Arg-Pro-Phe-Leu-Leu-
Arg-Asn-Pro-Asn-Asp-Lys-Tyr-Glu-Pro-Phe-Glu-Glu-Tyr-Leu-
Gln (SEQ ID NO:25)

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
      (A) LENGTH: 27 amino acids

```
        (B) TYPE: amino acid
        (C) STRANDEDNESS:
        (D) TOPOLOGY: linear (ii) MOLECULE TYPE: peptide (v) FRAGMENT TYPE: C-terminal (ix) FEATURE:
        (A) NAME/KEY: Modified-site
        (B) LOCATION:2..6
        (D) OTHER INFORMATION:/product= "Xaa"
            /label= Xaa
            /note= "Pos 2: Xaa = Pro, Leu
            Pos 3: Xaa = Gly, Val, Pro
            Pos 4: Xaa = Lys, Val, Arg, Gly, Glu
            Pos 5: Xaa = Ala, Val, Gly, Leu, Ile
            Pos 6: Xaa = Gly, Phe, Trp, Tyr, Val"

(ix) FEATURE:
        (A) NAME/KEY: Modified-site
        (B) LOCATION:9..18
        (D) OTHER INFORMATION:/product= "Xaa"
            /label= Xaa
            /note= "Pos 10: Xaa = Phe, Tyr, Trp
            Pos 11: Xaa = Leu, Ala, Gly, Ile, Ser, Met
            Pos 12: Xaa = Leu, Ala, Gly, Ile, Ser, Met;
            Pos 13: Xaa = Arg, Lys,
            Pos 18: Xaa = Phe, Tyr"

(xi) SEQUENCE DESCRIPTION: SEQ ID NO: 1:

Ser Xaa Xaa Xaa Xaa Xaa Pro Arg Pro Xaa Xaa Xaa Xaa Asn Pro Gly
1               5                  10                  15

Asp Xaa Glu Glu Ile Pro Glu Glu Tyr Leu Gln
            20                  25

(2) INFORMATION FOR SEQ ID NO: 2:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (v) FRAGMENT TYPE: C-terminal (ix) FEATURE:
        (A) NAME/KEY: Modified-site
        (B) LOCATION:2..4
        (D) OTHER INFORMATION:/product= "Xaa"
            /label= Xaa
            /note= "Pos 3: Xaa = Phe, Tyr"

(xi) SEQUENCE DESCRIPTION: SEQ ID NO: 2:

Gly Asp Xaa Glu Glu Ile Pro Glu Glu Tyr Leu Gln
1               5                  10

(2) INFORMATION FOR SEQ ID NO: 3:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (v) FRAGMENT TYPE: C-terminal (xi) SEQUENCE DESCRIPTION: SEQ ID NO: 3:

Asn Asp Lys Tyr Glu Pro Phe Glu Glu Tyr Leu Gln
```

```
            1               5                   10
```

(2) INFORMATION FOR SEQ ID NO: 4:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (v) FRAGMENT TYPE: C-terminal (xi) SEQUENCE DESCRIPTION: SEQ ID NO: 4:

```
Ser Asp Phe Glu Glu Phe Ser Leu Asp Asp Ile Glu Gln
1               5                   10
```

(2) INFORMATION FOR SEQ ID NO: 5:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (v) FRAGMENT TYPE: C-terminal (xi) SEQUENCE DESCRIPTION: SEQ ID NO: 5:

```
Ser Glu Phe Glu Glu Phe Glu Ile Asp Glu Glu Glu Lys
1               5                   10
```

(2) INFORMATION FOR SEQ ID NO: 6:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O105"

(iii) HYPOTHETICAL: NO (iv) ANTI-SENSE: NO (xi) SEQUENCE DESCRIPTION: SEQ ID NO: 6:

```
TATGAGCAAA ACTTGCTACG AAGGTAACGG TCACTTCTAC CGTGGTAAGG CTTCTACCGA      60

CAC                                                                   63
```

(2) INFORMATION FOR SEQ ID NO: 7:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O106"

(iii) HYPOTHETICAL: NO (iv) ANTI-SENSE: NO (xi) SEQUENCE DESCRIPTION: SEQ ID NO: 7:

```
CATGGTGTCG GTAGAAGCCT TACCACGGTA GAAGTGACCG TTACCTTCGT AGCAAGTTTT      60

GCTCA                                                                 65

(2) INFORMATION FOR SEQ ID NO: 8:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "Synthetic DNA;
            Nucleotide sequence for Oligo O220"

(iii) HYPOTHETICAL: NO (iv) ANTI-SENSE: NO (xi) SEQUENCE DESCRIPTION: SEQ ID NO: 8:

CGGTTAAGGC TTTCCCGAGG CCTGGTGGTG GTGGTAACGG TGACTTCGAA GAAATCCCGG      60

AAGAGTACCT GTGATAGGAT CAA                                             83

(2) INFORMATION FOR SEQ ID NO: 9:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "Synthetic DNA;
            Nucleotide sequence for Oligo O221"

(iii) HYPOTHETICAL: NO (iv) ANTI-SENSE: NO (xi) SEQUENCE DESCRIPTION: SEQ ID NO: 9:

CTAGTTGATC CTATCACAGG TACTCTTCCG GGATTTCTTC GAAGTCACCG TTACCACCAC      60

CACCAGGCCT CGGGAAAGCC TTAACCGGGC T                                    91

(2) INFORMATION FOR SEQ ID NO: 10:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "Synthetic DNA;
            Nucleotide sequence for Oligo O265"

(iii) HYPOTHETICAL: NO (iv) ANTI-SENSE: NO (xi) SEQUENCE DESCRIPTION: SEQ ID NO: 10:

CACCCGGCGG AGACGGCGGG CTCAGAGCCA GACCGTTTTC TTCTTTGGTG TGAGAACG        58

(2) INFORMATION FOR SEQ ID NO: 11:

(i) SEQUENCE CHARACTERISTICS:
        (A) LENGTH: 58 base pairs
        (B) TYPE: nucleic acid
        (C) STRANDEDNESS: single
```

(D) TOPOLOGY: linear (ii) MOLECULE TYPE: other nucleic acid
        (A) DESCRIPTION: /desc = "Synthetic DNA;
            Nucleotide sequence for Oligo O281"

(iii) HYPOTHETICAL: NO (iv) ANTI-SENSE: NO (xi) SEQUENCE DESCRIPTION: SEQ ID NO: 11:

CGTCCGGGTG GTGGTGGTAA CGGTGACTTC GAAGAAATCC CGGAAGAATA CCTGTAAG        58

(2) INFORMATION FOR SEQ ID NO: 12:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O282"

(iii) HYPOTHETICAL: NO (iv) ANTI-SENSE: NO (xi) SEQUENCE DESCRIPTION: SEQ ID NO: 12:

GATCCGTTCT CACACCAAAG AAGAAAACGG TCTGGCTCTG AGCCCGCCGT CTCCGCCGGG        60

TGGTTTCCCG        70

(2) INFORMATION FOR SEQ ID NO: 13:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O283"

(iii) HYPOTHETICAL: NO (iv) ANTI-SENSE: NO (xi) SEQUENCE DESCRIPTION: SEQ ID NO: 13:

CTAGCTTACA GGTATTCTTC CGGGATTTCT TCGAAGTCAC CGTTACCACC ACCACCCGGA        60

CGCGGGAAAC        70

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O329"

(iii) HYPOTHETICAL: NO (iv) ANTI-SENSE: NO (xi) SEQUENCE DESCRIPTION: SEQ ID NO: 14:

```
AGAAATCCC GGAAGAATAC CTGCAATAAG                                              30

(2) INFORMATION FOR SEQ ID NO: 15:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O330"

(iii) HYPOTHETICAL: NO (iv) ANTI-SENSE: NO (xi) SEQUENCE DESCRIPTION: SEQ ID NO: 15:

CGGTTAAGGC CTTGGGGACC GCGGCCGCTG GGTGGTGGTG GTAACGGTGA CTTCG                 55

(2) INFORMATION FOR SEQ ID NO: 16:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O331"

(iii) HYPOTHETICAL: NO (iv) ANTI-SENSE: NO (xi) SEQUENCE DESCRIPTION: SEQ ID NO: 16:

ACCACCACCC AGCGGCCGCG GTCCCCAAGC CTTAACCGGG CT                               42

(2) INFORMATION FOR SEQ ID NO: 17:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O332"

(iii) HYPOTHETICAL: NO (iv) ANTI-SENSE: NO (xi) SEQUENCE DESCRIPTION: SEQ ID NO: 17:

CTAGCTTATT GCAGGTATTC TTCCGGGATT TCTTCGAAGT CACCGTTACC                       50

(2) INFORMATION FOR SEQ ID NO: 18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA;
            Nucleotide sequence for Oligo O347"

(iii) HYPOTHETICAL: NO
```

(iv) ANTI-SENSE: NO (xi) SEQUENCE DESCRIPTION: SEQ ID NO: 18:

CGGTTGTTGC TTTCCCGC                                                          18

(2) INFORMATION FOR SEQ ID NO: 19:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA;
                Nucleotide sequence for Oligo O348"

(iii) HYPOTHETICAL: NO (iv) ANTI-SENSE: NO (xi) SEQUENCE DESCRIPTION: SEQ ID NO: 19:

GGCCGCGGGA AAGCAACAAC CGGGCT                                                 26

(2) INFORMATION FOR SEQ ID NO: 20:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA;
                Nucleotide sequence for Oligo O545"

(iii) HYPOTHETICAL: NO (iv) ANTI-SENSE: NO (xi) SEQUENCE DESCRIPTION: SEQ ID NO: 20:

CTAGCTTATT GCAGGTATTC TTCGAACGGT TCGTATTTGT CGTTAGGGTT ACGCAGCAGG            60

AAA                                                                          63

(2) INFORMATION FOR SEQ ID NO: 21:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA;
                Nucleotide sequence for Oligo O546"

(iii) HYPOTHETICAL: NO (iv) ANTI-SENSE: NO (xi) SEQUENCE DESCRIPTION: SEQ ID NO: 21:

GGCCTTTCCT GCTGCGTAAC CCTAACGACA AATACGAACC GTTCGAAGAA TACCTGCAAT            60

AAC                                                                          63

(2) INFORMATION FOR SEQ ID NO: 22:

(i) SEQUENCE CHARACTERISTICS:
            (A) LENGTH: 63 base pairs (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA;
                Nucleotide sequence for Oligo O615"

(iii) HYPOTHETICAL: NO (iv) ANTI-SENSE: NO (xi) SEQUENCE DESCRIPTION: SEQ ID NO: 22:

CTAGCTTATT GCAGGTATTC TTCCGGGATT TCTTCGAAGT CACCAGGGTT ACGCAGCAGG      60

AAA                                                                    63

(2) INFORMATION FOR SEQ ID NO: 23:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA;
                Nucleotide sequence for Oligo O618"

(iii) HYPOTHETICAL: NO (iv) ANTI-SENSE: NO (xi) SEQUENCE DESCRIPTION: SEQ ID NO: 23:

GGCCTTTCCT GCTGCGTAAC CCTGGTGACT TCGAAGAAAT CCCGGAAGAA TACCTGCAAT      60

AAG                                                                    63

(2) INFORMATION FOR SEQ ID NO: 24:

(i) SEQUENCE CHARACTERISTICS:
            (A) LENGTH: 393 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO: 24:

Met Ser Lys Thr Cys Tyr Glu Gly Asn Gly His Phe Tyr Arg Gly Lys
1               5                   10                  15

Ala Ser Thr Asp Thr Met Gly Arg Pro Cys Leu Pro Trp Asn Ser Ala
            20                  25                  30

Thr Val Leu Gln Gln Thr Tyr His Ala His Arg Ser Asp Ala Leu Gln
        35                  40                  45

Leu Gly Leu Gly Lys His Asn Tyr Cys Arg Asn Pro Asp Asn Arg Arg
    50                  55                  60

Arg Pro Trp Cys Tyr Val Gln Val Gly Leu Lys Pro Leu Val Gln Glu
65                  70                  75                  80

Cys Met Val His Asp Cys Ala Asp Gly Lys Lys Pro Ser Ser Pro Pro
                85                  90                  95

Glu Glu Leu Lys Phe Gln Cys Gly Gln Lys Thr Leu Arg Pro Arg Phe
            100                 105                 110

Lys Ile Ile Gly Gly Glu Phe Thr Thr Ile Glu Asn Gln Pro Trp Phe
        115                 120                 125

Ala Ala Ile Tyr Arg Arg His Arg Gly Gly Ser Val Thr Tyr Val Cys

```
            130                 135                 140
Gly Gly Ser Leu Ile Ser Pro Cys Trp Val Ile Ser Ala Thr His Cys
145                 150                 155                 160

Phe Ile Asp Tyr Pro Lys Lys Glu Asp Tyr Ile Val Tyr Leu Gly Arg
                165                 170                 175

Ser Arg Leu Asn Ser Asn Thr Gln Gly Glu Met Lys Phe Glu Val Glu
                180                 185                 190

Asn Leu Ile Leu His Lys Asp Tyr Ser Ala Asp Thr Leu Ala His His
                195                 200                 205

Asn Asp Ile Ala Leu Leu Lys Ile Arg Ser Lys Glu Gly Arg Cys Ala
210                 215                 220

Gln Pro Ser Arg Thr Ile Gln Thr Ile Cys Leu Pro Ser Met Tyr Asn
225                 230                 235                 240

Asp Pro Gln Phe Gly Thr Ser Cys Glu Ile Thr Gly Phe Gly Lys Glu
                245                 250                 255

Asn Ser Thr Asp Tyr Leu Tyr Pro Glu Gln Leu Lys Met Thr Val Val
                260                 265                 270

Lys Leu Ile Ser His Arg Glu Cys Gln Gln Pro His Tyr Tyr Gly Ser
                275                 280                 285

Glu Val Thr Thr Lys Met Leu Cys Ala Ala Asp Pro Gln Trp Lys Thr
290                 295                 300

Asp Ser Cys Gln Gly Asp Ser Gly Gly Pro Leu Val Cys Ser Leu Gln
305                 310                 315                 320

Gly Arg Met Thr Leu Thr Gly Ile Val Ser Trp Gly Arg Gly Cys Ala
                325                 330                 335

Leu Lys Asp Lys Pro Gly Val Tyr Thr Arg Val Ser His Phe Leu Pro
                340                 345                 350

Trp Ile Arg Ser His Thr Lys Glu Glu Asn Gly Leu Ala Leu Ser Pro
                355                 360                 365

Val Val Ala Phe Pro Arg Pro Phe Leu Leu Arg Asn Pro Gly Asp Phe
                370                 375                 380

Glu Glu Ile Pro Glu Glu Tyr Leu Gln
385                 390

(2) INFORMATION FOR SEQ ID NO: 25:

(i) SEQUENCE CHARACTERISTICS:
        (A) LENGTH: 393 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 25:

Met Ser Lys Thr Cys Tyr Glu Gly Asn Gly His Phe Tyr Arg Gly Lys
1               5                   10                  15

Ala Ser Thr Asp Thr Met Gly Arg Pro Cys Leu Pro Trp Asn Ser Ala
                20                  25                  30

Thr Val Leu Gln Gln Thr Tyr His Ala His Arg Ser Asp Ala Leu Gln
            35                  40                  45

Leu Gly Leu Gly Lys His Asn Tyr Cys Arg Asn Pro Asp Asn Arg Arg
        50                  55                  60

Arg Pro Trp Cys Tyr Val Gln Val Gly Leu Lys Pro Leu Val Gln Glu
65                  70                  75                  80

Cys Met Val His Asp Cys Ala Asp Gly Lys Lys Pro Ser Ser Pro Pro
```

-continued

```
                   85                  90                  95
Glu Glu Leu Lys Phe Gln Cys Gly Gln Lys Thr Leu Arg Pro Arg Phe
                100                 105                 110

Lys Ile Ile Gly Gly Glu Phe Thr Thr Ile Glu Asn Gln Pro Trp Phe
            115                 120                 125

Ala Ala Ile Tyr Arg Arg His Arg Gly Gly Ser Val Thr Tyr Val Cys
        130                 135                 140

Gly Gly Ser Leu Ile Ser Pro Cys Trp Val Ile Ser Ala Thr His Cys
145                 150                 155                 160

Phe Ile Asp Tyr Pro Lys Lys Glu Asp Tyr Ile Val Tyr Leu Gly Arg
                165                 170                 175

Ser Arg Leu Asn Ser Asn Thr Gln Gly Glu Met Lys Phe Glu Val Glu
            180                 185                 190

Asn Leu Ile Leu His Lys Asp Tyr Ser Ala Asp Thr Leu Ala His His
            195                 200                 205

Asn Asp Ile Ala Leu Leu Lys Ile Arg Ser Lys Glu Gly Arg Cys Ala
        210                 215                 220

Gln Pro Ser Arg Thr Ile Gln Thr Ile Cys Leu Pro Ser Met Tyr Asn
225                 230                 235                 240

Asp Pro Gln Phe Gly Thr Ser Cys Glu Ile Thr Gly Phe Gly Lys Glu
                245                 250                 255

Asn Ser Thr Asp Tyr Leu Tyr Pro Glu Gln Leu Lys Met Thr Val Val
            260                 265                 270

Lys Leu Ile Ser His Arg Glu Cys Gln Gln Pro His Tyr Tyr Gly Ser
            275                 280                 285

Glu Val Thr Thr Lys Met Leu Cys Ala Ala Asp Pro Gln Trp Lys Thr
        290                 295                 300

Asp Ser Cys Gln Gly Asp Ser Gly Gly Pro Leu Val Cys Ser Leu Gln
305                 310                 315                 320

Gly Arg Met Thr Leu Thr Gly Ile Val Ser Trp Gly Arg Gly Cys Ala
                325                 330                 335

Leu Lys Asp Lys Pro Gly Val Tyr Thr Arg Val Ser His Phe Leu Pro
            340                 345                 350

Trp Ile Arg Ser His Thr Lys Glu Glu Asn Gly Leu Ala Leu Ser Pro
            355                 360                 365

Val Val Ala Phe Pro Arg Pro Phe Leu Leu Arg Asn Pro Asn Asp Lys
        370                 375                 380

Tyr Glu Pro Phe Glu Glu Tyr Leu Gln
385                 390
```

CHIMERIC PROTEINS HAVING FIBRINOLYTIC AND THROMBIN-INHIBITING PROPERTIES

This application is a continuation of application Ser. No. 08/563,649 filed on Nov. 28, 1995.

BACKGROUND OF THE INVENTION

This invention relates to chimeric proteins having fibrinolytic and thrombin-inhibiting properties, which are linked at the C-terminal end of the plasminogen-activating amino acid sequence to a thrombin-inhibiting amino acid sequence. The invention also relates to plasmids for producing these polypeptides and to thrombolytic agents which contain a polypeptide of this type as their active ingredient.

In all industrialized countries, cardio-circulatory diseases currently constitute the most frequent cause of death. Particularly important in this respect are acute thrombotic occlusions, the occurrence of which in the case of coronary thrombosis leads within a very short time to a life-threatening under-supply of the cardiac muscle. Similar considerations apply to cerebral thrombosis, intracerebral occlusions being accompanied here by massive ischemic damage to the brain areas concerned. In contrast to coronary thrombosis, which is associated with high mortality rates, under-supply in cerebral thrombosis does not as a rule lead to life-threatening situations, but to severe impairment of an everyday way of life due to the failure of certain brain functions, and thus leads in part to a drastic loss of quality of life for those affected. It is generally true for both these forms of thrombosis that within a few hours—without therapy—the regions supplied by the arteries concerned are irreversibly damaged. Other thrombotic occlusion diseases which require treatment include pulmonary embolism, venous thrombosis and peripheral arterial occlusion diseases.

The occlusion of a blood vessel caused by a thrombus mainly occurs at an arteriosclerotic lesion comprising fibrin, thrombocytes and erythrocytes under the action of various enzymes of the blood coagulation system. Within the enzyme cascade of the coagulation system, thrombin plays a prominent role. Thrombin can activate all the important enzymes of the coagulation system, can induce the aggregation of thrombocytes and can lead to the formation of a fibrin network by the conversion of fibrinogen to fibrin (Furie and Furie in New Engl. J. Med. 326, 800 (1992)).

The formation of thromboses is restricted by physiological anticoagulants, for example antithrombin III, activated protein C and tissue factor pathway inhibitor. Once formed, thromboses can be re-dissolved by the action of plasmin occurring naturally in the body. Plasmin is formed from an inactive proenzyme, plasminogen, which is proteolytically activated by plasminogen activators. The thrombolysis due to plasmin is utilized therapeutically, by treating patients with thrombotic diseases, particularly patients with acute coronary thrombosis, with plasminogen activators. The aim of therapeutic intervention is to reduce the infarct and to lower the mortality rate. Streptokinase, APSAC (anisolated plasminogen streptokinase activator complex), double-chain urokinase (UK), recombinant single-chain urokinase (recombinant prourokinase) and tissue plasminogen activator (t-PA) are currently available for this therapy (Collen and Lijnen in Blood 78, 3114, (1991)). It clearly follows from the experiences of lysis therapy which have been published hitherto that re-opening of the occluded coronary vessels within a few hours, i.e. 1 to 4 hours after the occurrence of the coronary, provides the best functional results. In order to achieve the aim of optimum reperfusion, therapy in the majority of cases should actually be commenced even before admission as an in-patient. However, this is only possible using a fibrinolytic agent which has few side effects and which is safe, and in view of the diagnosis situation also, which is still uncertain at this time. When employed in the requisite doses for the treatment of acute coronary disease, however, all fibrinolytic agents of the so-called first generation, such as streptokinase, APSAC and urokinase, produce a generalized plasminogen activation which is accompanied by a high risk of hemorrhage. Even the use of fibrinolytic agents of the so-called second generation, t-PA and prourokinase, leads to systemic plasminogen activation in many coronary patients. For successful reperfusion and to prevent re-occlusions, both t-PA and prourokinase have to be used in high doses, which result in significant fibrinogenolysis, and therefore to systemic plasminogen activation. This is in agreement with the observation that in previous studies no significant differences could be detected in the frequency of hemorrhage complications between patients treated with tPA or prourokinase and patients treated with streptokinase.

Various approaches have therefore been pursued aimed at improving the pharmacological profile of plasminogen activators. The following are under development: bat plasminogen activators (Gardell et al. in J. Biol. Chem. 264, 17947 (1989); Australian Patent No. AU 642,404-B (=EP 383,417), staphylokinase (Schlott et al. in Bio/Technology 12, 185 (1994); Collen and Van De Werf in Circulation 87, 1850 (1993)), the recombinant tissue plasminogen activator BM 06.022 (Martin et al. in J. Cardiovasc. Pharm. 18, 111 (1991)) and the t-PA variant TNK-t-PA (Keyt et al. in Proc. Natl. Acad. Sci. 91, 3670 (1994)).

Streptokinase, a protein of hemolytic Streptococci, activates human plasminogen, in that it forms a complex with plasminogen and thereby converts the plasminogen into an active conformation. This complex itself converts free plasminogen to plasmin, which then in turn cleaves the plasminogen bound to streptokinase. Staphylokinase, a protein obtained from *Staphylococcus aureus,* also acts similarly, but possesses a higher fibrin specificity compared with streptokinase. APSAC, a compound of streptokinase and human plasminogen which is produced in vitro, is a further development of streptokinase. Due to a chemical modification of the active center of the plasminogen, APSAC has a biological half-life which is longer than that of streptokinase.

Urokinase is a human protein which can be obtained in two forms as a proteolytically active protein from urine; high molecular weight urokinase (HUK) and low molecular weight urokinase (LUK) (Stump et al. in J. Biol. Chem. 261, 1267 (1986)). HUK and LUK are active forms of urokinase, i.e. double-chain molecules. Urokinase is formed as single-chain urokinase (prourokinase) in various tissues and can be detected in small amounts as a proenzyme in human blood (Wun et al. in J. Biol. Chem. 257, 3276 (1982)). As HUK, the activated form of prourokinase has a molecular weight of 54 kilodaltons and consists of 3 domains: the amino-terminal growth factor domain, the kringle domain and the serine protease domain (Guenzler et al. in Hoppe-Seyler's Z. Physiol. Chem. 363, 1155 (1982); Steffens et al. in Hoppe-Seyler's Z. Physiol. Chem. 363, 1043 (1982)). Although prourokinase and plasminogen are present as proenzymes, prourokinase is capable, due to its intrinsic activity, of transforming plasminogen into active plasmin. However, this plasminogen activator does not attain its full activity until the plasmin formed has itself cleaved the prourokinase between [158]lysine and [159]isoleucine (Lijnen et al. in J. Biol. Chem. 261, 1253 (1986)). The production of urokinase in *Escherichia coli* by genetic engineering was first described by Heyneker et al. (Proceedings of the IVth International Symposium on Genetics of Industrial Microorganisms 1982). Unglycosylated prourokinase (saruplase) is produced using a synthetic gene (Brigelius-Flohe' et al. in Appl. Microbiol. Biotech. 36, 640 (1992)).

t-PA is a protein with a molecular weight of 72 kilodaltons which is present in blood and in tissue. This plasminogen activator consists of 5 domains: the amino-terminal finger domain, the growth factor domain, kringle domain 1, kringle domain 2 and the serine protease domain. Like prourokinase, t-PA is converted into the active, double-chain form by a plasmin-catalyzed cleavage between kringle domain 2 and the serine protease domain, i.e. between [275]Arg and [276]Ile. In vitro studies and the results of experiments on animals indicate that t-PA binds to fibrin and its enzymatic activity is stimulated by fibrin (Collen and Lijnen in Blood 78, 3114 (1991)). The fibrin specificity of t-PA should prevent the formation of plasmin in the entire blood system, resulting not only in the decomposition of fibrin decomposed but also in the decomposition of fibrinogen. A systemic plasminogen activation such as this as well as the extensive decomposition of fibrinogen are undesirable, since this increases the risk of hemorrhage. It has been shown in therapeutic practice, however, that the expectations derived from pre-clinical studies as regards the fibrin specificity of t-PA are not fulfilled. Due to the short biological half-life of t-PA it is necessary to infuse high doses, which result in systemic plasminogen activation despite this fibrin specificity (Keyt et al. in Proc. Natl. Acad. Sci. 91, 3670 (1994)).

r-PA and TNK-t-PA are variants of t-PA which possess improved properties. In r-PA (BM 06.022) the first three t-PA domains, i.e. the finger domain, the growth factor domain and the first kringle domain, have been deleted, so that the shortened molecule only contains the second kringle domain and the protease domain. r-PA is produced in *Escherichia coli* by genetic engineering and is not glycosylated. Compared with t-PA, r-PA has a longer biological half-life and more rapidly leads to reperfusion. It has been shown in experiments on animals that r-PA applied as a bolus is just as effective as a t-PA infusion (Martin et al. in J. Cardiovasc. Pharmacol. 18, 111 (1991)).

The t-PA variant TNK-t-PA differs from natural t-PA on three counts: the replacement of [103]threonine by asparagine, due to which a new glycosylation site is formed; the replacement of [117]asparagine by glutamine, due to which a glycosylation site is removed, and the replacement of the sequence between [296]lysine and [299]arginine by four successive alanine units. The combination of these three mutations results in a polypeptide with a higher fibrin specificity and a longer biological half-life compared with natural t-PA. Moreover, TNK-t-PA is considerably less inhibited by PAI-1 than is natural t-PA (Keyt et al. in Proc. Natl. Acad. Sci. 91, 3670 (1994)). Results obtained from experiments on animals in which a precursor of TNK-t-PA was used indicate that TNK-t-PA is suitable for bolus application (Refino et al. in Thromb. Haemost. 70, 313 (1993)).

Bat plasminogen activator (bat-PA) occurs in the saliva of the *Desmodus rotundus* bat. This plasminogen activator, which has meanwhile also been synthesized by genetic engineering, has an even more pronounced fibrin specificity than t-PA and in tests on animals has exhibited improved thrombolysis with an increased biological half-life and reduced systemic plasminogen activation (Gardell et al. in Circulation 84, 244 (1991)).

In the treatment of thrombotic diseases, plasminogen activators are generally administered together with an anticoagulant substance, for example heparin. This results in improved thrombolysis compared to treatment with only a plasminogen activator (Tebbe et al. in Z. Kardiol. 80, Suppl. 3, 32 (1991)). Various clinical results indicate that, in parallel with the dissolution of thromboses, an increased tendency towards coagulation occurs (Szczeklik et al. in Arterioscl. Thromb. 12, 548 (1992); Goto et al. in Angiology 45, 273 (1994)). It is assumed that thrombin molecules which are enclosed in the thrombus and which are released again when the clot dissolves are responsible for this. Moreover, there are indications that plasminogen activators themselves also accelerate the activation of prothrombin and thus act in opposition to thrombolysis (Brommer and Meijer in Thromb. Haemostas. 70, 995 (1993)). Anticoagulant substances such as heparin, hirugen, hirudin, argatroban, protein C and recombinant tick anticoagulant peptide (TAP) can suppress this increased tendency towards re-occlusion during thrombolysis and can thus enhance the success of lysis therapy (Yao et al. in Am. J. Physiol. 262 (Heart Circ. Physiol. 31) H 347–H 379 (1992); Schneider in Thromb. Res. 64, 667 (1991); Gruber et al. in Circulation 84, 2454 (1991); Martin et al. in J. Am. Coll. Cardiol. 22, 914 (1993); Vlasuk et al. in Circulation 84, Suppl. II-467 (1991).

One of the strongest thrombin inhibitors is hirudin from the *Hirudo medicinales* leech, which consists of 65 amino acids. There are various iso-forms of hirudin, which differ as regards some of their amino acids. All iso-forms of hirudin block the binding of thrombin to a substrate, for example fibrinogen, and also block the active center of thrombin (Rydel et al. in Science 249, 277 (1990); Bode and Huber in Molecular Aspects of Inflammation, Springer, Berlin, Heidelberg, 103–115 (1991); Stone and Hofsteenge in Prot. Engineering 2, 295 (1991); Dodt et al. in Biol. Chem. Hoppe-Seyler 366, 379 (1985). In addition, smaller molecules derived from hirudin are known, which also act as thrombin inhibitors (Maraganore et al. in Biochemistry 29, 7095 (1990); Krstenansky et al. in J. Med. Chem. 30, 1688 (1987); Yue et al. in Prot. Engineering 5, 77 (1992)).

The use of hirudin in combination with a plasminogen activator for the treatment of thrombotic diseases is described in U.S. Pat. No. 4,944,943 (=EP 328,957) and U.S. Pat. No. 5,126,134 (=EP 365,468). The use of hirudin derivatives in combination with a thrombolytic agent is known from PCT International Patent Application WO 91/01142.

Hirullin is a protein containing 61 amino acids which is isolated from the *Hirudo manillensis* leech. Hirullin is identical to hirudin as regards its action and inhibitor strength, but differs very considerably from hirudin as regards its amino acid sequence. It has also proved possible to derive smaller molecules from hirullin, which are very good thrombin inhibitors (Krstenansky et al. in Febs Lett. 269, 465 (1990)).

In addition, thrombin can also be inhibited by a peptide which is derived from the amino-terminal sequence of the human thrombin receptor (Vu et al. in Nature 253, 674 (1991)). The thrombin receptor contains a thrombin-binding sequence, with an adjacent cleavage site for thrombin, in the extracellular, amino-terminal region. This sequence can inhibit thrombin provided that the cleavage site is masked by the replacement of [42]serine by [42]phenylalanine.

Phaneuf et al., in Thromb. Haemost. 71, 481 (1994), describe a complex which results from a fortuitous chemical linking of streptokinase and hirudin. The plasminogen-activating capacity of this streptokinase-hirudin complex is less than that of unmodified streptokinase by a factor of 8, however.

As noted above, plasminogen-activating amino acid sequences contain various domain sites which are well known and are described in the literature.

Urokinase and prourokinase comprise the following domains:

| Domain | Amino Acids Included |
|---|---|
| Growth Factor Domain | amino acids 1 to 43 |
| Kringle Domain | amino acids 50 to 131 |
| Serine Protease Domain | amino acids 158 to 411 |

See Guenzler et al., "The Primary Structure of High Molecular Mass Urokinase form Human Urine; The Complete Amino Acid Sequence of the A Chain", *Hoppe-Seyler's Z. Physiol. Chem.*, 363, 1:55–65 (1982); Steffens et al., "The Complete Amino Acid Sequence of Low Molecular Mass Urokinase from Human Urine", *Hoppe-Seyler's Z. Physiol. Chem.*, 363, 1043–1058 (1982).

Tissue plasminogen activator comprises the following domains:

| Domain | Amino Acids Included |
|---|---|
| Finger Domain | amino acids 4 to 50 |
| Growth Factor Domain | amino acids 50 to 87 |
| Kringle 1 Domain | amino acids 87 to 176 |
| Kringle 2 Domain | amino acids 176 to 262 |
| Serine Protease Domain | amino acids 276 to 527 |

See Collen et al., "Thrombolytic and Pharmacokinetic Properties of Human Tissue-Type Plasminogen Activator Variants Obtained by Deletion and/or Duplication of Structural/Functional Domains, in a Hamster Pulmonary Embolism Model", *Thrombosis and Haeomostasis*, 65, (2), 174–180 (1991).

Bat-plasminogen activator comprises the following domains:

| Domain | Amino Acids Included |
|---|---|
| Finger Domain | amino acids 1 to 43 |
| Growth Factor Domain | amino acids 44 to 84 |
| Kringle Domain | amino acids 92 to 173 |
| Serine Protease Domain | amino acids 189 to 441 |

See Gardell et al., "Isolation, Characterization, and cDNA Cloning of a Vampire Eat Salivary Plasminogen Activator", *Journal of Biological Chem-st-y*, 264, (30), 17947–952 (1989).

SUMMARY OF THE INVENTION

The underlying object of the present invention was to provide active ingredients for the treatment of vascular diseases caused by thrombosis, Which effect complete thrombolysis within a very short period and which at the same time prevent vascular re-occlusion after what is first of all a successful thrombolysis.

Another object of the invention was to provide a way to prevent systemic plasminogen activation by means of these active ingredients.

In accordance with the present invention it has now been found that the considerable demands imposed on such active ingredients can be fulfilled by chimeric proteins having fibrinolytic properties which contain a thrombin-inhibiting amino acid sequence at the C-terminal end of the plasminogen-activating amino acid sequence.

Accordingly, the present invention relates to chimeric proteins having fibrinolytic and thrombin-inhibiting properties, which are linked at the C-terminal end of the plasminogen-activating amino acid sequence to an amino acid sequence of formula I Ser-$X_1$-$X_2$-$X_3$-$X_4$-$X_5$-Pro-Arg-Pro-$Y_1$-$Y_2$-$Y_3$-$Y_4$-Asn-Pro-Z (SEQ ID NO: 1),
in which $X_1$ represents Pro or Leu; $X_2$ represents Gly, Val or Pro; $X_3$ represents Lys, Val, Arg, Gly or Glu; $X_4$ represents Ala, Val, Gly, Leu or Ile; $X_5$ represents Gly, Phe, Trp, Tyr or Val; $Y_1$ represents Phe, Tyr or Trp; $Y_2$ represents Leu, Ala, Gly, Ile, Ser or Met; $Y_3$ represents Leu, Ala, Gly, Ile, Ser or Met; $Y_4$ represents Arg, Lys or His, and Z represents the amino acid sequence of formula II Gly-Asp-$Z_1$-Glu-Glu-Ile-Pro-Glu-Glu-Tyr-Leu-Gln (SEQ ID NO: 2),
in which $Z_1$ represents Phe or Tyr,
or of formula III Asn-Asp-Lys-Tyr-Glu-Pro-Phe-Glu-Glu-Tyr-Leu-Gln (SEQ ID NO: 3),
or of formula IV Ser-Asp-Phe-Glu-Glu-Phe-Ser-Leu-Asp-Asp-Ile-Glu-Gln (SEQ ID NO: 4),
or of formula V Ser-Glu-Phe-Glu-Glu-Phe-Glu-Ile-Asp-Glu-Glu-Lys (SEQ ID NO: 5).

The chimeric proteins according to the invention bind to thrombin via the thrombin-inhibiting amino acid sequence of formula I, due to which high concentrations of chimeric protein are attained at the clot. Since the clots formed in acute coronary or cerebral thrombosis are rich in thrombin, the thrombus specificity of the proteins according to the invention provides the possibility of increasing the thrombolytic efficacy and selectivity of the plasminogen activators. Systemic plasminogen activation and fibrinogenolysis are thereby prevented and the level of safety of the active ingredients is considerably enhanced. Due to the thrombus specificity, the dose can also be reduced compared with conventional plasminogen activators, which again enhances the safety of the preparation. At the same time it can be anticipated that the dosage of the anticoagulant co-medication (e.g. containing heparin) can be reduced when using the proteins according to the invention. Further, it is also possible to dispense with an additional anticoagulant.

Preferred chimeric proteins contain as their plasminogen-activating amino acid sequence the unaltered amino acid sequence of prourokinase, at least one modified prourokinase amino acid sequence having a serine protease domain exhibiting at least 90%, and preferably at least 95%, sequence identity to the serine protease domain of the unaltered amino acid sequence of prourokinase, the unaltered amino acid sequence of urokinase, at least one modified urokinase amino acid sequence having a serine protease domain exhibiting at least 90%, and preferably at least 95%, sequence identity to the serine protease domain of the unaltered amino acid sequence of urokinase, the unaltered amino acid sequence of tissue plasminogen activator (t-PA), at least one modified t-PA amino acid sequence having a serine protease domain exhibiting at least 90%, and preferably at least 95%, sequence identity to the serine protease domain of the unaltered amino acid sequence of t-PA, the unaltered amino acid sequence of bat plasminogen activator (bat-PA), at least one modified bat-PA amino acid sequence having a serine protease domain exhibiting at least 90%, and preferably at least 95%, sequence identity to the serine protease domain of the unaltered amino acid sequence of bat-PA, and/or the amino acid sequence of streptokinase, staphylokinase and/or APSAC. As used herein, the term "modified" amino acid sequence refers to an amino acid sequence which has been altered by deletion, substitution, insertion and/or addition. Such deletions, substitutions, insertions and/or additions may be effected by conventional techniques which are known to persons skilled in the genetic engineering art.

In particular, the plasminogen-activating amino acid sequence in the proteins according to the invention contains the unaltered amino acid sequence of prourokinase, at least one modified prourokinase amino acid sequence having a serine protease domain exhibiting at least 90%, and preferably at least 95%, sequence identity to the serine protease domain of the unaltered amino acid sequence of prourokinase, the unaltered amino acid sequence of t-PA and/or at least one modified t-PA amino acid sequence having a serine protease domain exhibiting at least 90%, and preferably at least 95%, sequence identity to the serine protease domain of the unaltered amino acid sequence of t-PA.

In preferred embodiments of the invention, the plasminogen-activating amino acid sequence comprises a modified sequence which includes at least one kringle domain exhibiting at least 90% sequence identity to the corresponding kringle domain of the corresponding unaltered sequence, and a serine protease domain exhibiting at least 90% sequence identity to the corresponding serine protease domain of the corresponding unaltered sequence.

Proteins are particularly preferred -n which the plasminogen-activating amino acid sequence comprises at least one of the sequence of prourokinase which consists of 411 amino acids and in which the amino acid in position 407 is Asn or Gln, or the $^{47}$Ser to $^{411}$Leu amino acid sequence of prourokinase in which the amino acid in position 407 is Asn or Gln; or the $^{138}$Ser to $^{411}$Leu amino acid sequence of prourokinase in which the amino acid in position 407 is Asn or Gln; or the unaltered sequence of t-PA which consists of 527 amino acids; or the Ser-$^{89}$Arg to $^{527}$Pro amino acid sequence of t-PA, or the $^{174}$Ser to $^{527}$Pro amino acid sequence of t-PA.

In the chimeric proteins, the plasminogen-activating amino acid sequence at the C-terminal end is preferably linked to a thrombin-inhibiting amino acid sequence of formula I, in which $X_1$ represents Pro; $X_2$ represents Val; $X_3$ represents Lys or Val; $X_4$ represents Ala, and $X_5$ represents Phe. In the amino acid sequence of formula I, $Y_1$ preferably represents Phe; $Y_2$ preferably represents Leu; $Y_3$ preferably represents Leu, and $Y_4$ preferably represents Arg. In particular, the variable Z in the amino acid sequence of formula I represents an amino acid sequence of formula II or formula IV.

Compared with known plasminogen activators, or with known mixtures comprising a plasminogen activator and a thrombin inhibitor, or with the known streptokinase-hirudin complex, the proteins according to the invention are distinguished by a stronger fibrinolytic effect combined with surprisingly good thrombin-inhibiting properties. In addition, plasma fibrinogen is consumed in considerably smaller amounts by the polypeptides according to the invention. The effect of the significantly higher fibrin specificity which results from this, particularly by comparison even with the known mixtures comprising a plasminogen activator and a thrombin inhibitor, is that the coagulation capacity of the blood is only slightly affected and the risk of uncontrolled hemorrhages as possible complications of systemic fibrinogen decomposition is minimized. The high fibrin specificity of the proteins according to the invention thus permits bolus applications with a significantly reduced risk of hemorrhage compared with bolus applications of known thrombolytic agents.

Accordingly, the present invention also relates to thrombolytic agents which contain a protein according to the invention as their active ingredient.

From 0.1 to 1 mg of a polypeptide according to the invention is required per kg for the treatment of vascular occlusions caused by thrombosis, for example coronary thrombosis, cerebral thrombosis, peripheral acute arterial occlusion, pulmonary embolism, unstable angina pectoris and deep venous thrombosis of the legs and pelvis. The proteins according to the invention can be administered parenterally by bolus injection or infusion.

In addition to at least one polypeptide according to the invention, the thrombolytic agents according to the invention may contain auxiliary materials or adjuvants, for example carriers, solvents, diluents, colorants and binders. The choice of these auxiliary materials, as well as the amounts thereof to be used, depends on how the drug is to be administered, and is considered to be within the skill of the art.

The proteins according to the invention are produced using genetic engineering methods. For this purpose the corresponding genes from synthetic oligonucleotides are cloned into suitable plasmids and expressed in *Escherichia coli* under the control of the trp- or tac promoter, particularly under the control of the trp promoter.

Accordingly, the present invention also relates to plasmids for use in the production of chimeric proteins which plasmids comprise operons which comprise a regulable promoter, a Shine-Dalgarno sequence which is effective as a ribosome binding site, a start codon, a synthetic structural gene for a protein according to the invention, and one or two terminators downstream of the structural gene.

The plasmids according to the invention can be expressed in *Escherichia coli* strains, particularly in *Escherichia coli* strains of group K 12, for example *E. coli* K 12 JM 101 (ATCC 33876), *E. coli* K 12 JM 103 (ATCC 39403), *E. coli* K 12 JM 105 (DSM 4162) and *E. coli* K 12 DH 1 (ATCC 33849). In the bacterial cell, the polypeptides according to the invention occur in high yield in inclusion bodies in which the protein exists in denatured form. After isolating the inclusion bodies the denatured protein is folded into the desired tertiary structure, by a protein chemistry technique, under the action of a redox system.

BRIEF DESCRIPTION OF THE DRAWINGS

The invention will be described in further detail hereinafter with reference to representative examples illustrated in the accompanying drawings in which:

FIG. 13 shows the amino acid sequence of peptide M37 (SEQ ID NO: 24); and

FIG. 14 shows the amino acid sequence of peptide M38 (SEQ ID NO: 25).

EXAMPLES

1. Preparation, isolation and purification of proteins according to the invention.

a) Cloning operations

Figure 1:
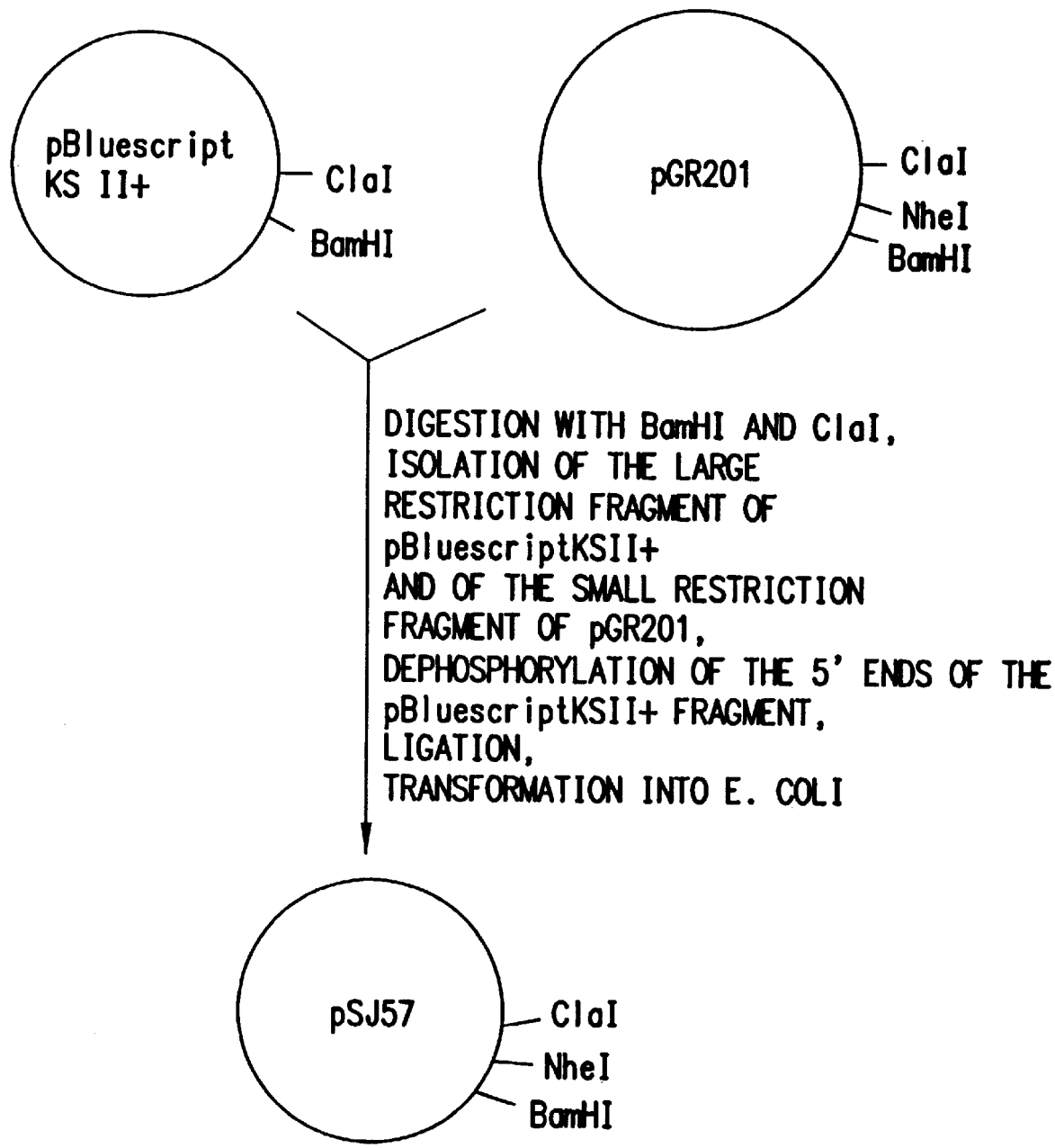
FIGS. 1 through 12 are schematic illustrations of the steps for preparing expression plasmids for producing the proteins of the present invention.
Figure 2:
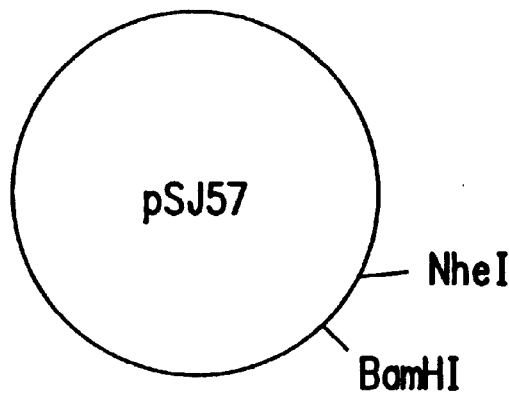
Figure 2:
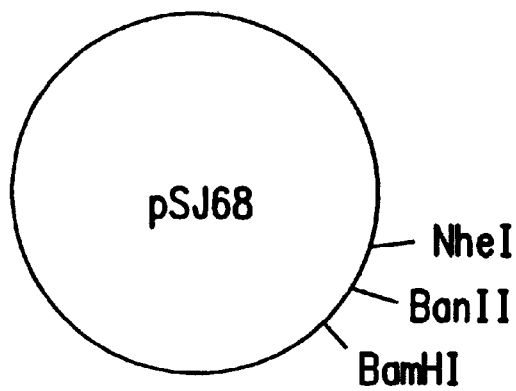
Figure 3:
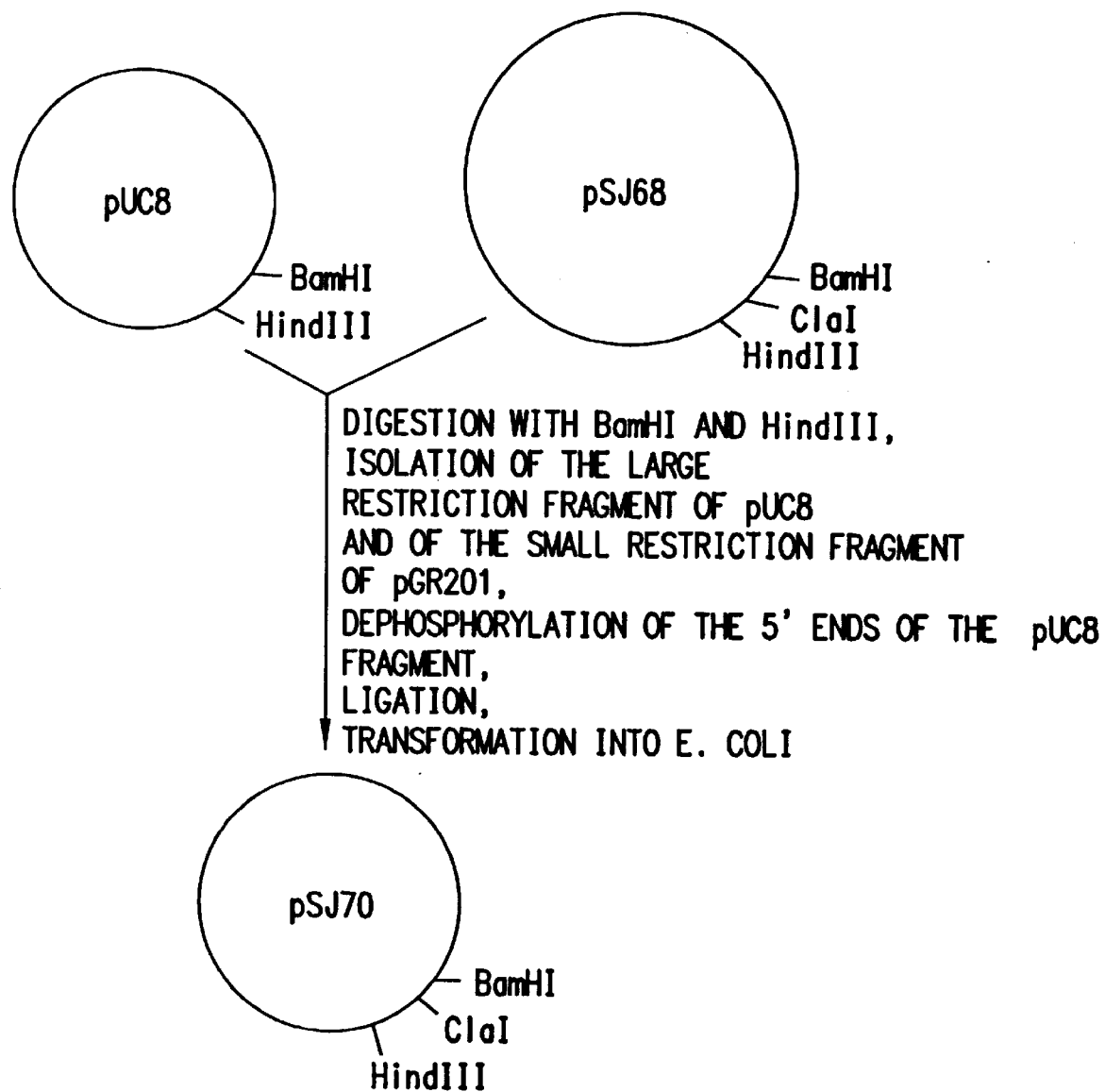
Figure 4:
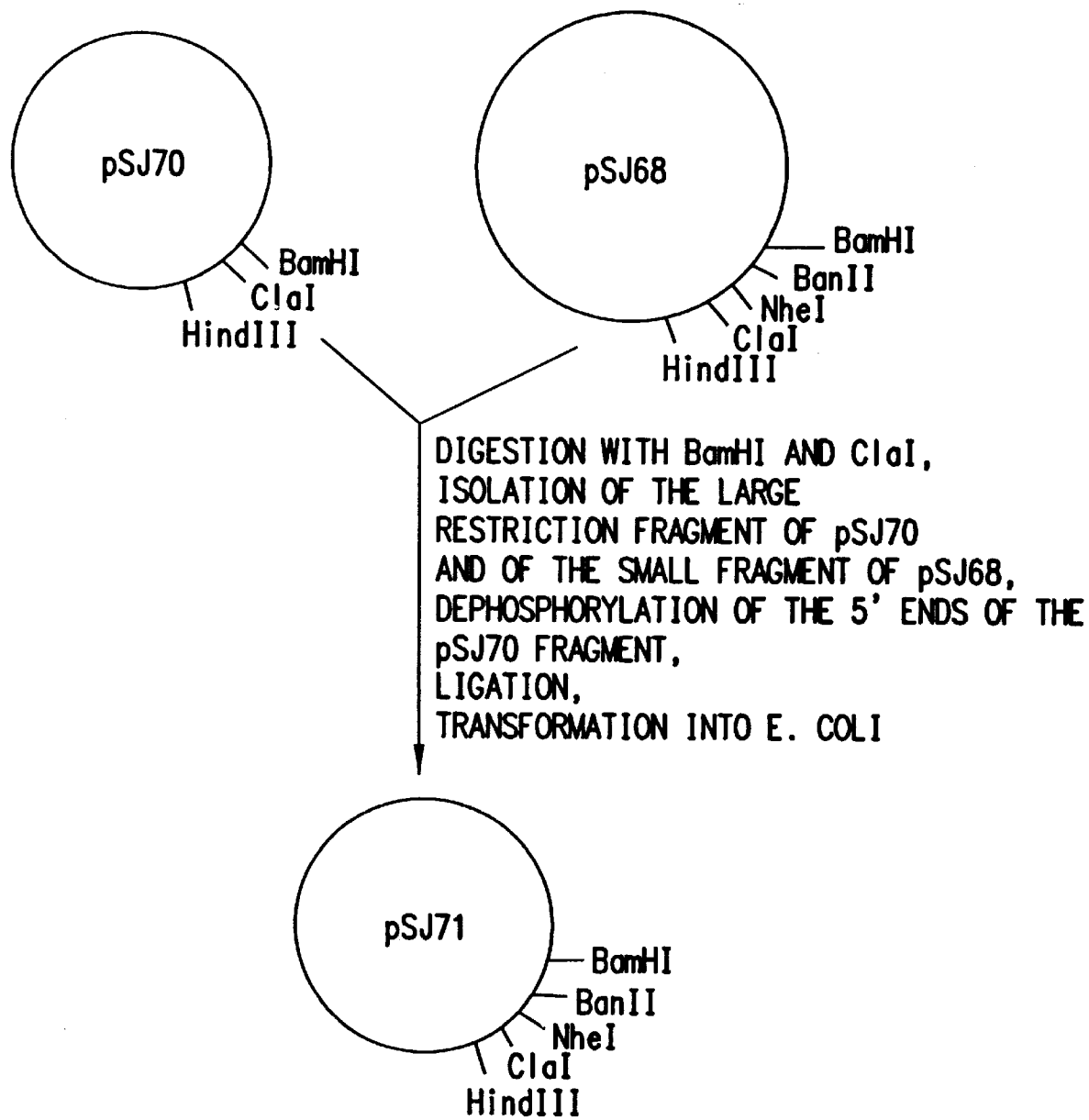
Figure 5:
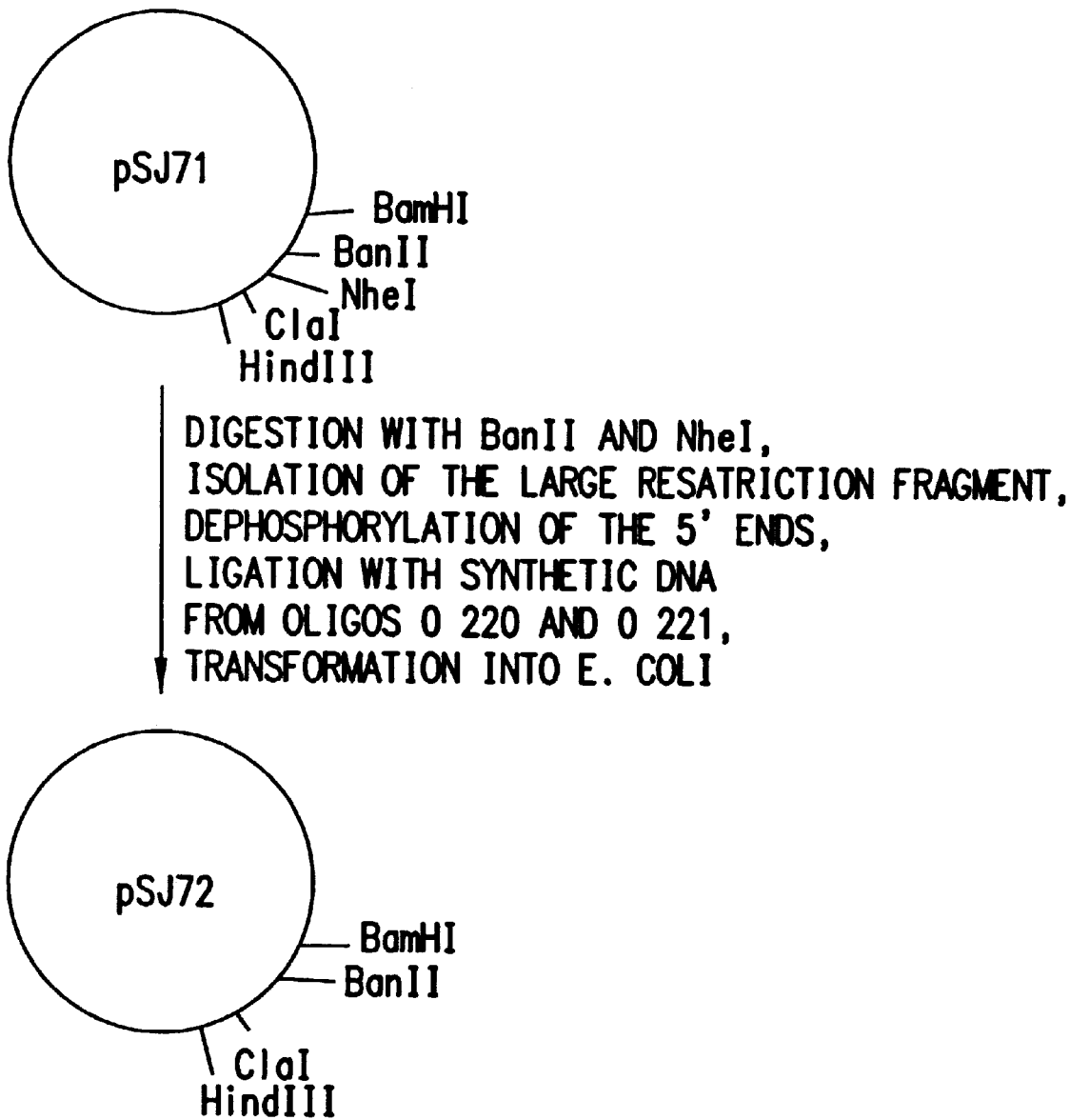
Figure 6:
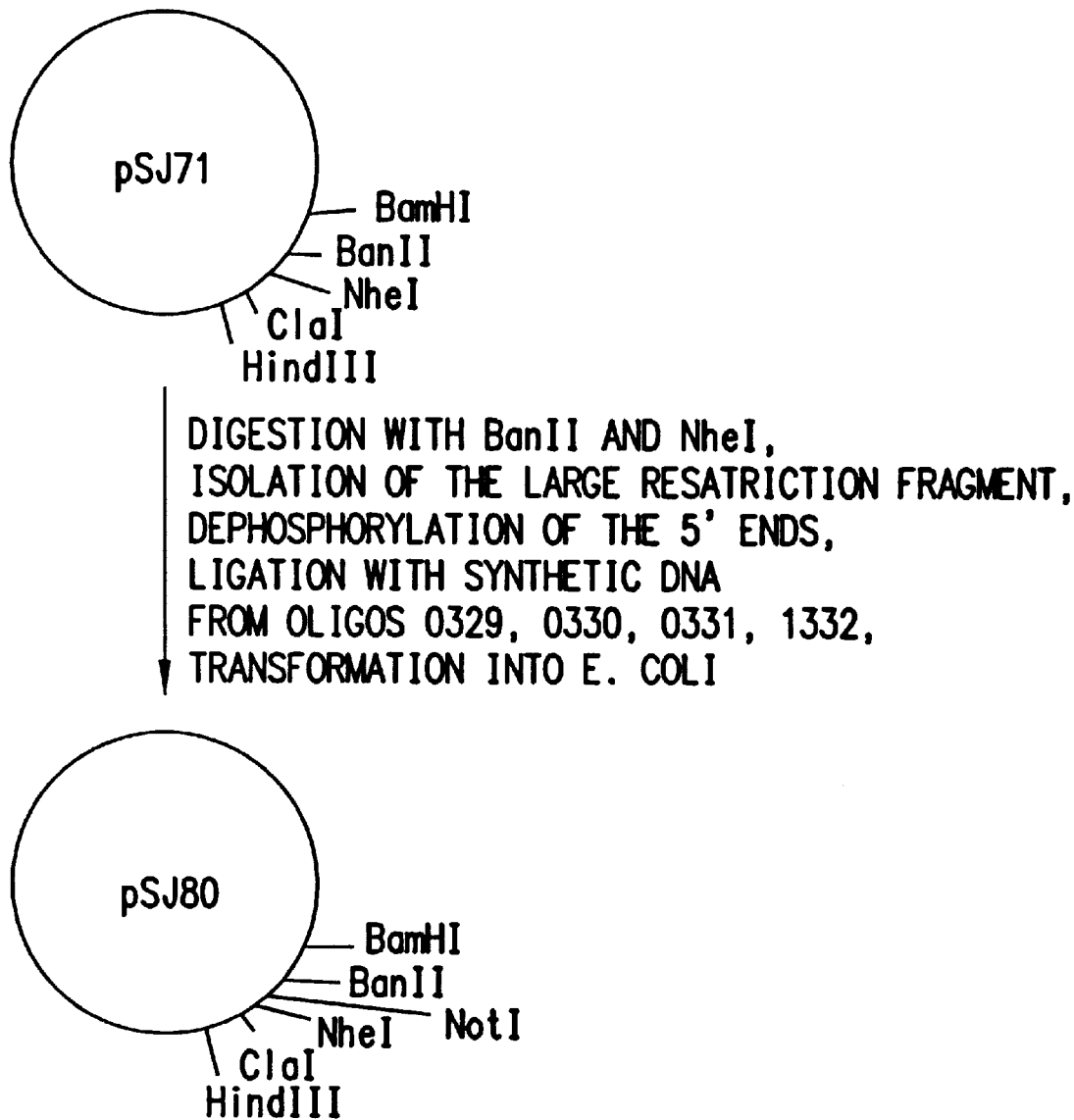
Figure 7:
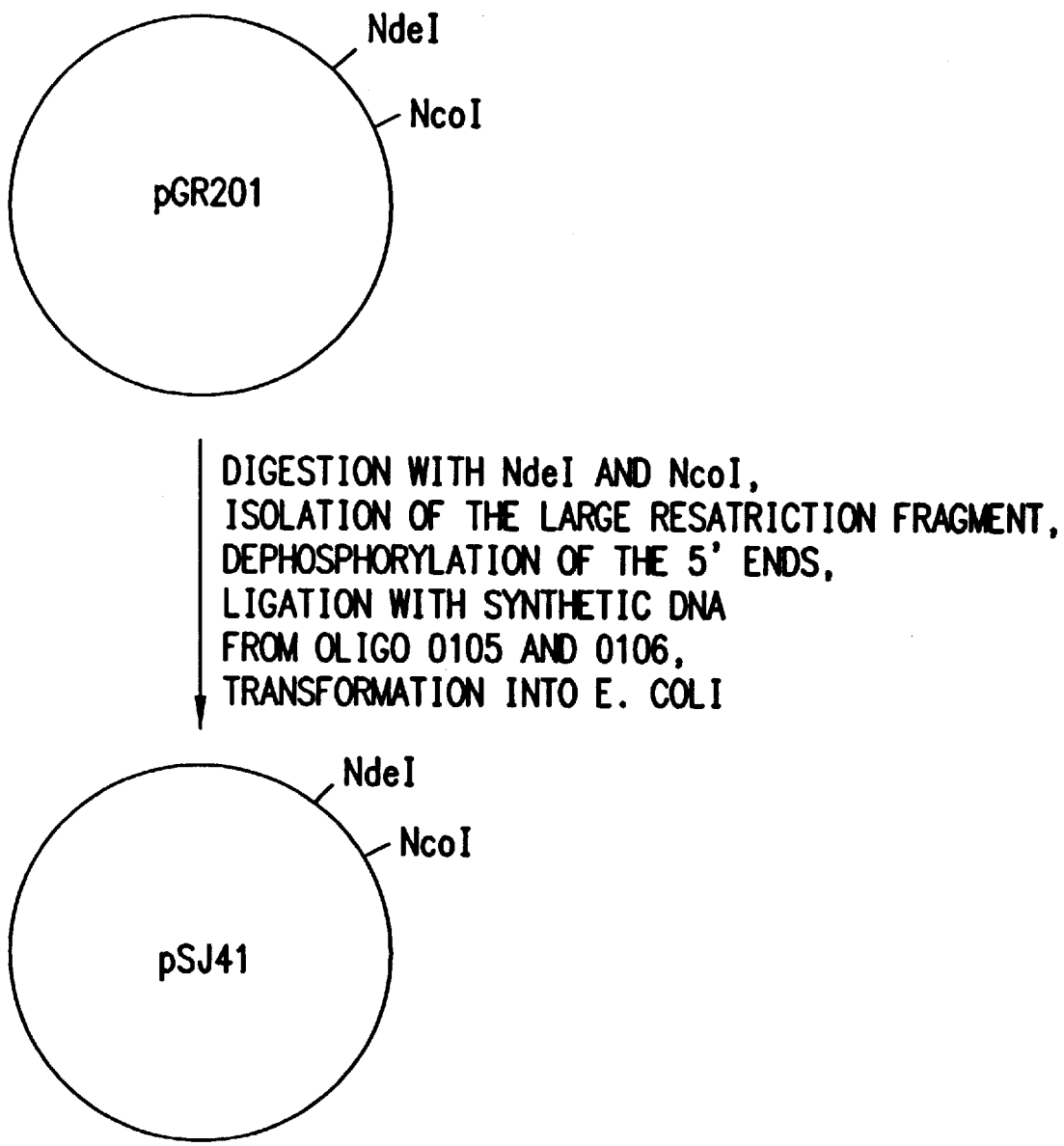
Figure 8:
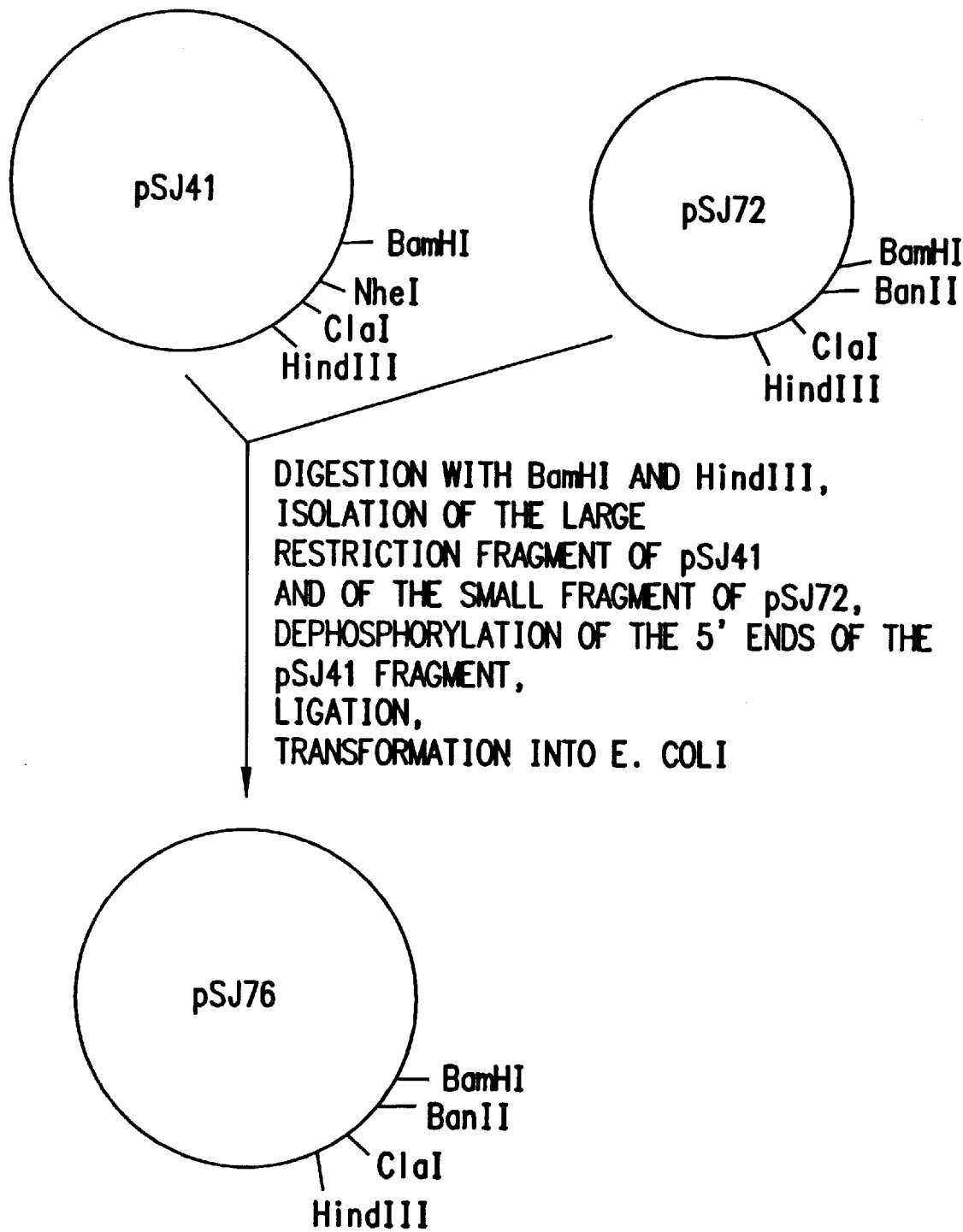
Figure 9:
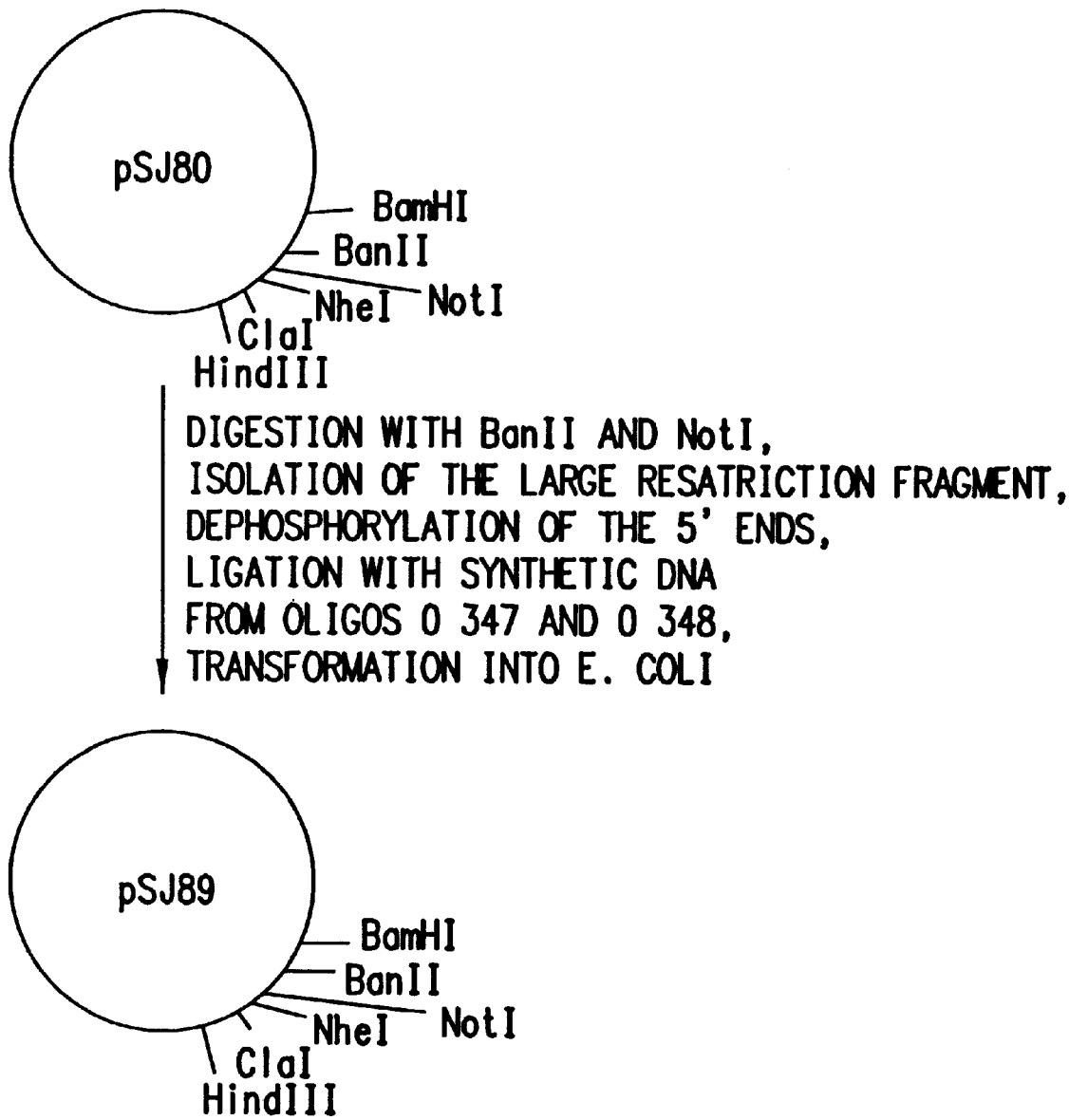
Figure 10:
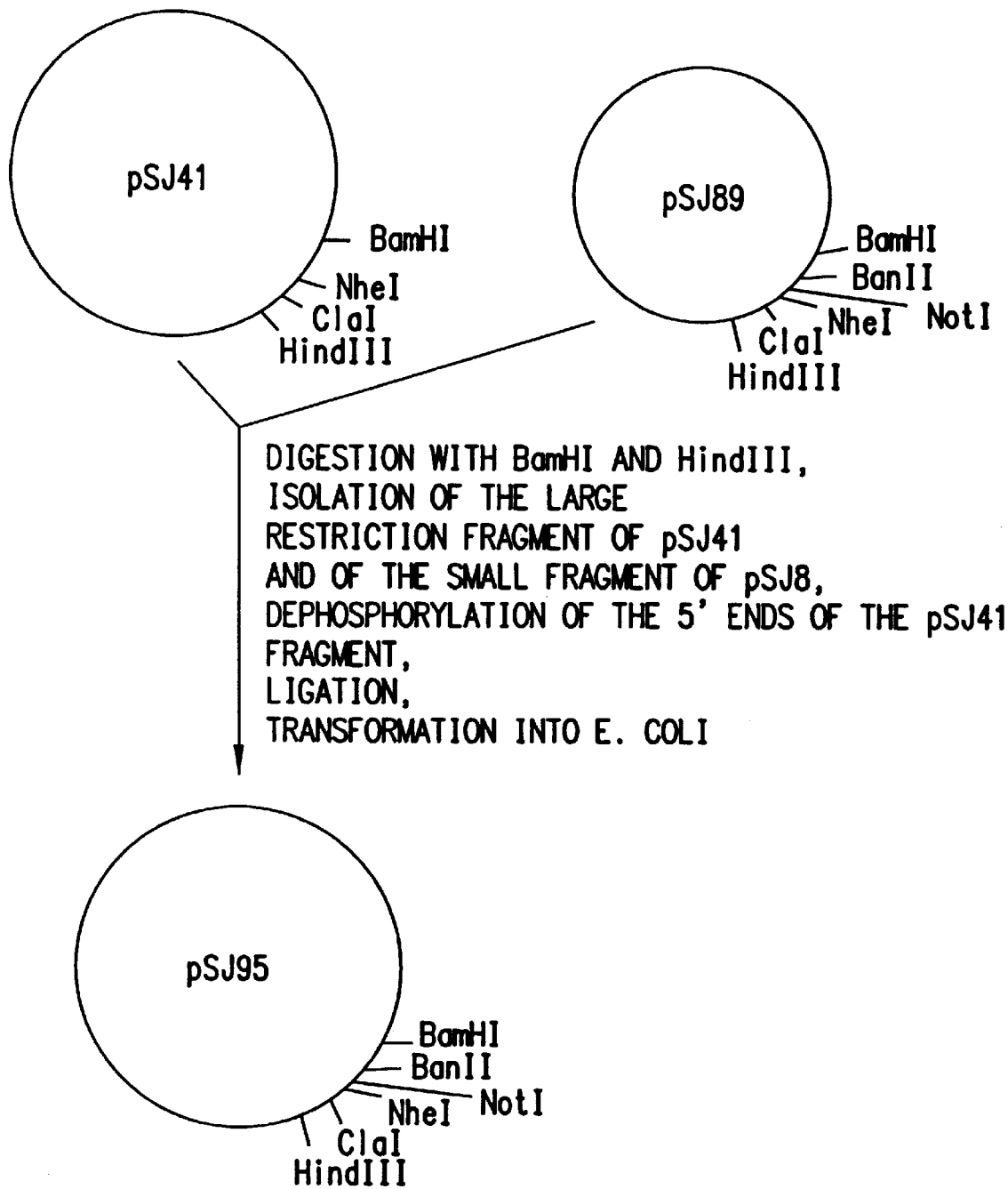
Figure 11:
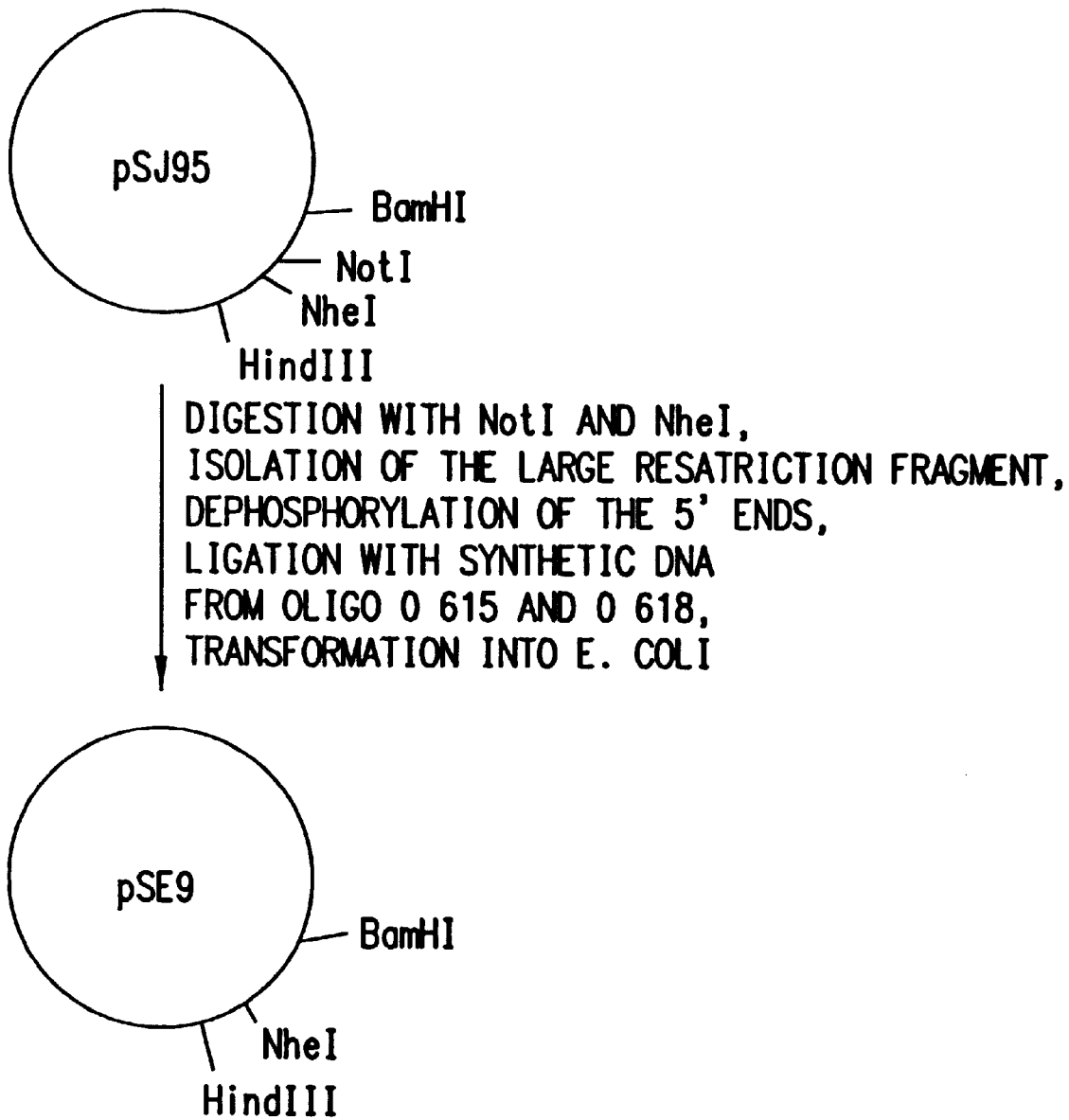
Figure 12:
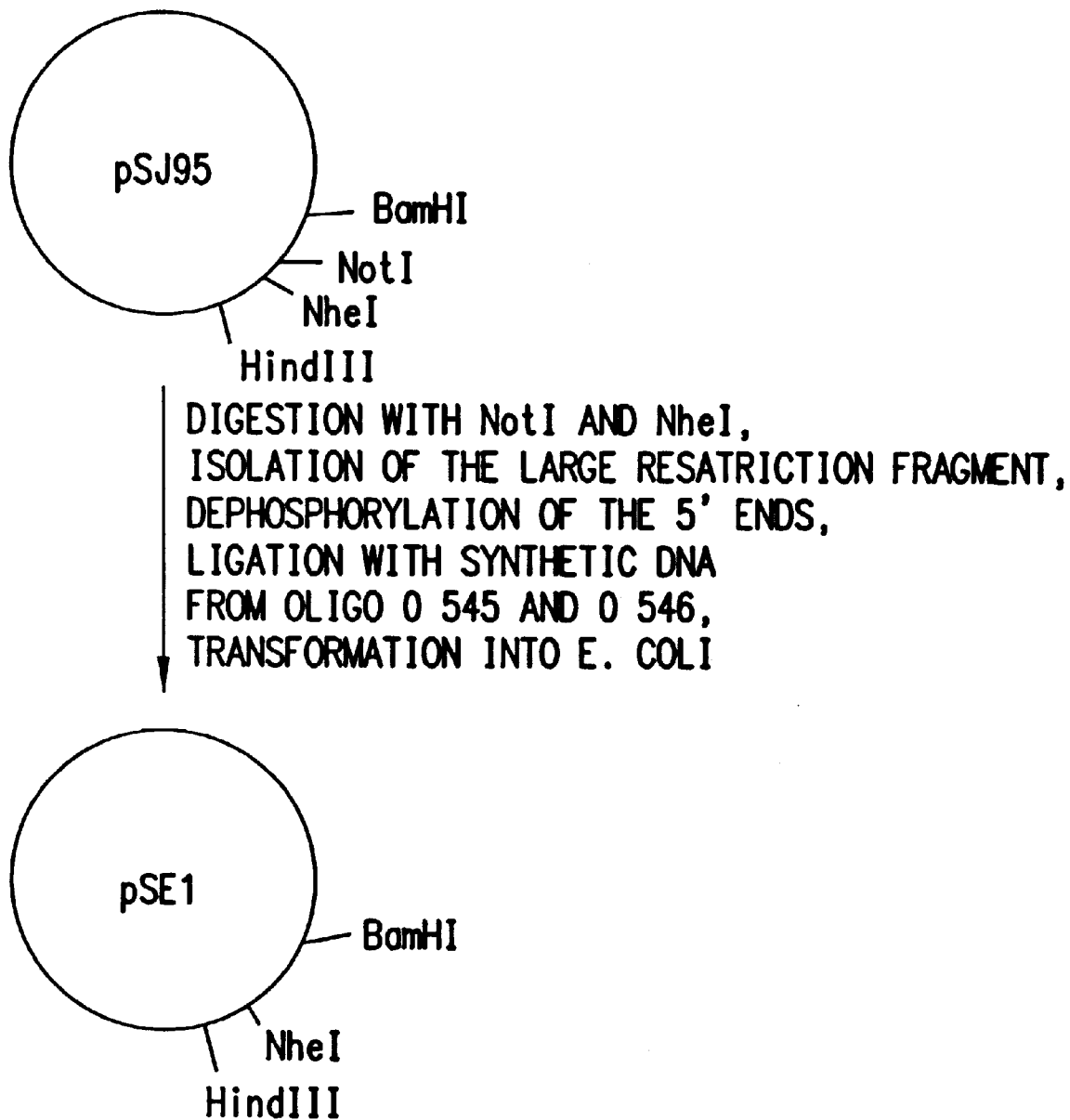

The expression plasmids for the production by genetic engineering of the polypeptides according to the invention in *Escherichia coli* were prepared in a manner known in the art. The sequence of the individual preparation steps is illustrated in FIGS. 1 to 12. The starting materials for the preparation of the plasmids were the plasmids pBluescript KS II+(manufactured by Stratagene, Heidelberg), pUC8 (manufactured by Pharmacia, Freiburg), and pGR201. pGR201 is identical to plasmid pSF160 described in Canadian Patent Application No. CA 2,020,656 (=EP 408, 945) and Appl. Microbiol. Biotechn. 36, 640–649 (1992). The restriction endonucleases BanII, BamHI, ClaI, HindIII, NcoI, NdeI, NheI, NotI, and the DNA-modifying enzymes such as the alkaline phosphatase, T4 ligase, T4 kinase and T7 polymerase, were obtained from the companies Pharmacia, Stratagene, Boehringer Mannheim and Gibco (Eggenstein). The changes in the plasmids during their preparation were verified by restriction analysis and DNA sequencing. DNA sequencing was effected according to the manufacturer's instructions, using a collection of reagents supplied by Pharmacia. Various oligodeoxyribonucleotides (oligos) were used in the preparation of the plasmids; their sequences, together with the associated designations, are given in Table 1.

The oligodeoxyribonucleotides were prepared in detritylated form on an 0.1 μmolar scale, by means of a synthesizer (Model 391) supplied by Applied Biosystems (Weiterstadt) according to the manufacturer's data, using β-cyanoethyl-protected diisopropylamino-phosphoamidites. 100 pmoles of each oligodeoxyribonucleotide were phosphorylated with one T4 kinase enzyme unit in the presence of 10 mM adenosine triphosphate in 50 mM tri(hydroxymethyl)amino-methane/HCl (tris-HCl), 10 mM magnesium chloride and 5 mM dithiothreitol at a pH of 7.5 and subsequently transformed to double-strand DNA molecules in the same buffer. The resulting synthetic double-strand DNA molecules were purified by gel electrophoresis on a polyacrylamide gel (5% polyacrylamide) and subsequently used in the ligation with the correspondingly prepared plasmids. Preparation of the plasmids by digestion with restriction enzymes, isolation of the corresponding restriction fragments and dephosphorylation of the 5'-ends, subsequent ligation and transformation into *E. coli* K12 JM103, as well as all other genetic engineering operations, were carried out in a known manner as described by Sambrook et al. in "Molecular Cloning: A Laboratory Manual", Second Edition, Cold Spring Harbor Laboratory Press, Cold Spring Harbor, USA, 1989.

TABLE 1

| Oligo | Sequence written from 5' to 3' |
|---|---|
| O 105 | TATGAGCAAAACTTGCTACGAAGGTAACGGTCACTTCTACCGTG GTAAGGCTTCTACCGACAC (SEQ ID NO:6) |
| O 106 | CATGGTGTCGGTAGAAGCCTTACCACGGTAGAAGTGACCGTTAC CTTCGTAGCAAGTTTTGCTCA (SEQ ID NO:7) |

TABLE 1-continued

| Oligo | Sequence written from 5' to 3' |
|---|---|
| O 220 | CGGTTAAGGCTTTCCCGAGGCCTGGTGGTGGTGGTAACGGTGAC TTCGAAGAAATCCCGGAAGAGTACCTGTGATAGGATCAA (SEQ ID NO:8) |
| O 221 | CTAGTTGATCCTATCACAGGTACTCTTCCGGGATTTCTTCGAAG TCACCGTTACCACCACCACCAGGCCTCGGGAAAGCCTTAACCGG GCT (SEQ ID NO:9) |
| O 265 | CACCCGGCGGAGACGGCGGGCTCAGAGCCAGACCGTTTTCTTCT TTGGTGTGAGAACG (SEQ ID NO:10) |
| O 281 | CGTCCGGGTGGTGGTGGTAACGGTGACTTCGAAGAAATCCCGGA AGAATACCTGTAAG (SEQ ID NO:11) |
| O 282 | GATCCGTTCTCACACCAAAGAAGAAAACGGTCTGGCTCTGAGCC CGCCGTCTCCGCCGGGTGGTTTCCCG (SEQ ID NO:12) |
| O 283 | CTAGCTTACAGGTATTCTTCCGGGATTTCTTCGAAGTCACCGTT ACCACCACCACCCGGACGCGGGAAAC (SEQ ID NO:13) |
| O 329 | AAGAAATCCCGGAAGAATACCTGCAATAAG (SEQ ID NO:14) |
| O 330 | CGGTTAAGGCTTGGGGACCGCGGCCGCTGGGTGGTGGTGGTAAC GGTGACTTCG (SEQ ID NO:15) |
| O 331 | ACCACCACCCAGCGGCCGCGGTCCCCAAGCCTTAACCGGGCT (SEQ ID NO:16) |
| O 332 | CTAGCTTATTGCAGGTATTCTTCCGGGATTTCTTCGAAGTCACC GTTACC (SEQ ID NO:17) |
| O 347 | CGGTTGTTGCTTTCCCGC (SEQ ID NO:18) |
| O 348 | GGCCGCGGGAAAGCAACAACCGGGCT (SEQ ID NO:19) |
| O 545 | CTAGCTTATTGCAGGTATTCTTCGAACGGTTCGTATTTGTCGTT AGGGTTACGCAGCAGGAAA (SEQ ID NO:20) |
| O 546 | GGCCTTTCCTGCTGCGTAACCCTAACGACAAATACGAACCGTTC GAAGAATACCTGCAATAAC (SEQ ID NO:21) |
| O 615 | CTAGCTTATTGCAGGTATTCTTCCGGGATTTCTTCGAAGTCACC AGGGTTACGCAGCAGGAAA (SEQ ID NO:22) |
| O 618 | GGCCTTTCCTGCTGCGTAACCCTGGTGACTTCGAAGAAATCCCG GAAGAATACCTGCAATAAG (SEQ ID NO:23) | b) Preparation of reusable cultures and fermentation

The recombinant expression plasmids pSEI (M 38) and pSE9 (M 37) were introduced into *E. coli* K12 JM103 (ATCC 39403) and spread out on standard I-nutrient agar (Merck, 150 mg/l ampicillin) (Sambrook et al. "Molecular Cloning: A Laboratory Manual"). A single colony of each transformation was cultivated in standard I-nutrient broth (Merck, pH 7.0; 150 mg/l ampicillin) at 20° C. to an optical density (OD) of 1 at 578 nm, and, with the addition of dimethyl sulfoxide (DMSO) (final concentration 7.5%), was frozen at and stored at −70° C. in 2 ml portions as a reusable culture. To produce the polypeptides according to the invention, 1 ml of each reusable culture was suspended in 20 ml standard I-nutrient broth (pH 7.0; 150 mg/l ampicillin) and cultivated at 37° C. to an OD of 1 at 578 nm.

The entire amount of culture obtained was then suspended in 1 liter of standard I-nutrient broth (pH 7.0; 150 mg/l ampicillin) and fermented in shaken flasks at 37° C. Induction was effected by adding 2 ml of indole-acrylacetic acid solution (60 mg in 2 ml ethanol) at an OD of 0.5 to 1 at 578 nm.

c) Expression testing

In order to test the expression rate, cells corresponding to 1 ml of a cell suspension with an OD of 1 at 578 nm were centrifuged directly before induction and every hour after induction (for a total of 6 hours). The sedimented cells were digested with lysozyme (1 mg lysozyme per ml in 50 mM tris-HCl buffer, pH 8.0, 50 mM ethylenediaminetetraacetic acid (EDTA) and 15% saccharose) The homogenate from the lysed cells was solubilized in 4–5 M guanidinium hydrochloride solution and after diluting to 1.2 M guanidinium hydrochloride and adding a reducing agent (glutathione or cysteine) was subjected to the folding reaction for 2–5 hours (Winkler et al., Biochemistry 25, 4041 to 4045 (1986)). The single-chain polypeptides according to the invention which were obtained were transformed into the corresponding double-chain molecules by the addition of plasmin, and the activity of the double-chain molecules was determined with the chromogen substrate pyro-Glu-Gly-Arg-p-nitroanilide. Activation of the polypeptides according to the invention with plasmin was effected in 50 mM tris-HCl buffer, 12 mM sodium chloride, 0.02% Tween 80 at pH 7.4 and 37° C. The ratio of polypeptide according to the invention to plasmin was about 8000–36,000 to 1, based on enzyme units. The test incubation was effected in 50 mM tris-HCl buffer and 38 mM sodium chloride at pH 8.8 in the presence of 0.36 µM aprotinine (to inhibit the plasmin) and 0.27 mM of pyro-Glu-Gly-Arg-p-nitroanilide substrate at 37° C. Depending on the concentration of the polypeptide according to the invention, the reaction was stopped after an incubation period of 5 to 60 minutes by adding 50% acetic acid, and the extinction at 405 nm was measured. According to the information from the manufacturer of the substrate (Kabi Vitrum, Sweden), in this procedure a change in extinction of 0.05 per minute at 405 nm corresponds to a urokinase activity of 25 ploug units per ml of test solution. The polypeptides according to the invention had specific activities between 120,000 and 155,000 ploug units per mg of protein. The protein content of the solutions was determined using the BCA assay of the Pierce company.

d) Isolation and purification

After 6 hours, the fermentation carried out under the conditions described in 1b) was terminated (density 5–6 CD at 578 nm) and the cells were extracted by centrifuging. The cell sediment was re-suspended in 200 ml water and digested in a high-pressure homogenizer. After renewed centrifugation, the sediment, which contained the entire amount of single-chain polypeptide according to the invention, was dissolved in 500 ml 5 M guanidinium hydrochloride, 40 mM cysteine, 1 mM EDTA at a pH of 8.0 and diluted with 2000 ml 25 mM tris-HCl with a pH of 9.0. The folding reaction was complete after about 12 hours.

After adding 8 g silica gel, the polypeptides according to the invention which were obtained were completely bound to silica gel by stirring for 2 hours. The loaded silica gel was separated and washed with acetate buffer (pH 4.0). The polypeptides were eluted with 0.5 M trimethylammonium chloride (TMAC) in 0.1 M acetate buffer (pH 4). After two chromatographic separations (copper chelate column and cation exchanger) the polypeptides were obtained in pure form. Their single-chain character was established by N-terminal sequence analysis.

The isolated polypeptides according to the invention, the amino acid sequences of which are given in FIGS. 13 and 14, exhibited no activity or only very slight activity (less than 1%) in a direct activity test with the chromogen substrate for urokinase. Full enzyme activity was only obtained after cleavage with plasmin (the conditions are given in Section 1c). The polypeptides according to the invention were accordingly expressed as single-chain proteins in E. coli K12 JM103.

2. Determination of the thrombin-inhibiting effect

The inhibitor effect of the polypeptides according to the invention was determined by measuring the thrombin time, by mixing 200 µl of a 1:10 dilution of human citrate plasma in veronal buffer with 50 µl of thrombin solution (0.2 units) and 50 µl of an aqueous solution containing 0.4–30 µg of a polypeptide according to the invention. The time to the formation of a fibrin network was then measured.

The thrombin time values listed in Table 2 were determined in the presence of prourokinase or of the proteins M 37 and M 38 according to the invention. In contrast to prourokinase, M 37 and M 38 prolong the thrombin time depending on their dosage, and thus act as coagulation inhibitors.

TABLE 2

| Protein [µg] | Thrombin Time [sec] | | |
|---|---|---|---|
| | Prourokinase | M 37 | M 38 |
| 0 | 31 | 32 | 32 |
| 0.4 | | 40 | |
| 0.8 | | 79 | |
| 1.2 | | 148 | |
| 1.6 | | 195 | |
| 2.0 | | 266 | |
| 4.0 | 31 | >300 | 58 |
| 8.0 | | | 81 |
| 12.0 | | | 104 |
| 16.0 | | | 130 |
| 20.0 | 33 | | 150 |
| 30.0 | 33 | | >300 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A chimeric protein with fibrinolytic and thrombin-inhibiting properties comprising a plasminogen-activating amino acid sequence which is linked at its C-terminal end to an amino acid sequence of the formula I Ser-$X_1$-$X_2$-$X_3$-$X_4$-$X_5$-Pro-Arg-Pro-$Y_1$-$Y_2$-$Y_3$-$Y_4$-Asn-Pro-Z    (I)

(SEQ ID NO: 1),
wherein
$X_1$ represents Pro or Leu;
$X_2$ represents Gly, Val or Pro;
$X_3$ represents Lys, Val, Arg, Gly or Glu;
$X_4$ represents Ala, Val, Gly, Leu or Ile;
$X_5$ represents Gly, Phe, Trp, Tyr or Val;

$Y_1$ represents Phe;
$Y_2$ represents Leu;
$Y_3$ represents Leu;
$Y_4$ represents Arg, and
Z represents at least one amino acid sequence selected from the group consisting of:

Gly-Asp-$Z_1$-Glu-Glu-Ile-Pro-Glu-Glu-Tyr-Leu-Gln    (II)

(SEQ ID NO: 2),
wherein $Z_1$ represents Phe or Tyr,

Asn-Asp-Lys-Tyr-Glu-Pro-Phe-Glu-Glu-Tyr-Leu-Gln    (III)

(SEQ ID NO: 3),

Ser-Asp-Phe-Glu-Glu-Phe-Ser-Leu-Asp-Asp-Ile-Glu-Gln    (IV)

(SEQ ID NO: 4), and

Ser-Glu-Phe-Glu-Glu-Phe-Glu-Ile-Asp-Glu-Glu-Glu-Lys    (V)

(SEQ ID NO: 5),
said plasminogen-activating sequence being selected from the group consisting of:
   the unaltered amino acid sequence of prourokinase,
   modified prourokinase amino acid sequences having a serine protease domain exhibiting at least 95% sequence identity to the serine protease domain of the unaltered amino acid sequence of prourokinase,
   the unaltered amino acid sequence of urokinase,
   modified urokinase amino acid sequences having a serine protease domain exhibiting at least 95% sequence identity to the serine protease domain of the unaltered amino acid sequence of urokinase,
   the unaltered amino acid sequence of tissue plasminogen activator (t-PA), and
   modified t-PA amino acid sequences having a serine protease domain exhibiting at least 95% sequence identity to the serine protease domain of the unaltered amino acid sequence of t-PA.

2. A protein according to claim 1, wherein the plasminogen-activating amino acid sequence comprises at least one amino acid sequence which includes a serine protease domain and is selected from the group consisting of:
   the unaltered amino acid sequence of prourokinase,
   modified prourokinase amino acid sequences having a serine protease domain exhibiting at least 95% sequence identity to the serine protease domain of the unaltered amino acid sequence of prourokinase,
   the unaltered amino acid sequence of t-PA, and
   modified t-PA amino acid sequences having a serine protease domain exhibiting at least 95% sequence identity to the serine protease domain of the unaltered amino acid sequence of t-PA.

3. A protein according to claim 2, wherein the plasminogen-activating amino acid sequence comprises at least one sequence selected from the group consisting of:
   the amino acid sequence of prourokinase consisting of 411 amino acids in which the amino acid in position 407 is Asn or Gln,
   the $^{47}$Ser to $^{411}$Leu amino acid sequence of prourokinase in which the amino acid in position 407 is Asn or Gln,
   the $^{138}$Ser to $^{411}$Leu amino acid sequence of prourokinase in which the amino acid in position 407 is Asn or Gln,
   the unaltered amino acid sequence of t-PA consisting of 527 amino acids,
   the Ser-$^{89}$Arg to 527Pro amino acid sequence of t-PA, and
   the $^{174}$Ser to $^{527}$Pro amino acid sequence of t-PA.

4. A protein according to claim 1, wherein in the amino acid sequence of formula I, $X_1$ represents Pro; $X_2$ represents Val; $X_3$ represents Lys or Val; $X_4$ represents Ala, and $X_5$ represents Phe.

5. A protein according to claim 1, wherein in the amino acid sequence of formula I, Z represents an amino acid sequence of formula II or an amino acid sequence of formula IV.

6. A chimeric protein with fibrinolytic and thrombin-inhibiting properties comprising a plasminogen-activating amino acid sequence which is linked at its C-terminal end to an amino acid sequence of the formula I Ser-$X_1$-$X_2$-$X_3$-$X_4$-$X_5$-Pro-Arg-Pro-$Y_1$-$Y_2$-$Y_3$-$Y_4$-Asn-Pro-Z    (I)

(SEQ ID NO: 1),
wherein
   $X_1$ represents Pro or Leu;
   $X_2$ represents Gly, Val or Pro;
   $X_3$ represents Lys, Val, Arg, Gly or Glu;
   $X_4$ represents Ala, Val, Gly, Leu or Ile;
   $X_5$ represents Gly, Phe, Trp, Tyr or Val;
   $Y_1$ represents Phe;
   $Y_2$ represents Leu;
   $Y_3$ represents Leu;
   $Y_4$ represents Arg; and
   Z represents at least one amino acid sequence selected from the group consisting of:

Gly-Asp-$Z_1$-Glu-Glu-Ile-Pro-Glu-Glu-Tyr-Leu-Gln    (II)

(SEQ ID NO: 2), wherein $Z_1$ represents Phe or Tyr,

Asn-Asp-Lys-Tyr-Glu-Pro-Phe-Glu-Glu-Tyr-Leu-Gln    (III)

(SEQ ID NO: 3),

Ser-Asp-Phe-Glu-Glu-Phe-Ser-Leu-Asp-Asp-Ile-Glu-Gln    (IV)

(SEQ ID NO: 4), and

Ser-Glu-Phe-Glu-Glu-Phe-Glu-Ile-Asp-Glu-Glu-Glu-Lys    (V)

(SEQ ID NO: 5),
said plasminogen-activating sequence comprising at least one amino acid sequence selected from the group consisting of:
   an unaltered amino acid sequence of prourokinase,
   a modified prourokinase amino acid sequence having at least 95% sequence identity to the unaltered amino acid sequence of prourokinase,
   an unaltered amino acid sequence of t-PA, and
   a modified t-PA amino acid sequence having at least 95% sequence identity to the unaltered amino acid sequence of t-PA.

7. A thrombolytic composition comprising a chimeric protein according to claim 1, and at least one conventional pharmaceutical carrier or adjuvant.

* * * * *